US011648388B2

(12) United States Patent
Siess et al.

(10) Patent No.: US 11,648,388 B2
(45) Date of Patent: May 16, 2023

(54) BLOOD PUMP

(71) Applicant: Abiomed Europe GMBH, Aachen (DE)

(72) Inventors: Thorsten Siess, Aachen (DE); Wolfgang Kerkhoffs, Aachen (DE); Peter Skrodsky, Aachen (DE); Jimpo Wang, Aachen (DE); Marius Grauwinkel, Aachen (DE)

(73) Assignee: ABIOMED EUROPE GMBH, Aachen (DE)

( * ) Notice: Subject to any disclaimer, the term of this patent is extended or adjusted under 35 U.S.C. 154(b) by 399 days.

(21) Appl. No.: 16/648,337

(22) PCT Filed: Sep. 14, 2018

(86) PCT No.: PCT/EP2018/074929
§ 371 (c)(1),
(2) Date: Mar. 18, 2020

(87) PCT Pub. No.: WO2019/057636
PCT Pub. Date: Mar. 28, 2019

(65) Prior Publication Data
US 2020/0330666 A1 Oct. 22, 2020

(30) Foreign Application Priority Data

Sep. 19, 2017 (EP) .................................... 17191940

(51) Int. Cl.
*A61M 60/419* (2021.01)
*A61M 60/13* (2021.01)
(Continued)

(52) U.S. Cl.
CPC .......... *A61M 60/419* (2021.01); *A61M 60/13* (2021.01); *A61M 60/139* (2021.01);
(Continued)

(58) Field of Classification Search
CPC . A61M 60/205; A61M 60/422; A61M 60/148
See application file for complete search history.

(56) References Cited

U.S. PATENT DOCUMENTS

| 6,042,347 A | 3/2000 | Scholl et al. |
| 2009/0112312 A1* | 4/2009 | LaRose ............... A61M 60/135 |
| | | 417/423.1 |

(Continued)

FOREIGN PATENT DOCUMENTS

| CN | 103591028 A | 2/2014 |
| JP | 2010136862 A | 6/2010 |

OTHER PUBLICATIONS

International Search Report and Written Opinion for Application No. PCT/EP2018/074929 dated Nov. 12, 2018.
(Continued)

*Primary Examiner* — Michael J D'Abreu
(74) *Attorney, Agent, or Firm* — Botos Churchill IP Law LLP

(57) ABSTRACT

An intravascular blood pump (1) comprises a pump casing (2) having a blood flow inlet (21) and a blood flow outlet (22), and an impeller (3) arranged in said pump casing (2) so as to be rotatable about an axis of rotation, wherein the impeller (3) has blades (31) sized and shaped for conveying blood from the blood flow inlet (21) to the blood flow outlet (22). The blood pump (1) further comprises a drive unit (104) for rotating the impeller (3), the drive unit (104) comprising a plurality of posts (140) arranged about the axis of rotation (10). Coil windings (47) around the posts are sequentially controllable so as to create a rotating magnetic field. The shaft portion (141) of each of the posts (140) comprises a soft magnetic material which is discontinuous in cross-section transverse to the longitudinal axis of the respective post (140).

26 Claims, 25 Drawing Sheets

(51) Int. Cl.
*A61M 60/216* (2021.01)
*A61M 60/139* (2021.01)
*A61M 60/865* (2021.01)
*A61M 60/82* (2021.01)
*A61M 60/508* (2021.01)

(52) U.S. Cl.
CPC ........ *A61M 60/216* (2021.01); *A61M 60/508* (2021.01); *A61M 60/82* (2021.01); *A61M 60/865* (2021.01)

(56) References Cited

U.S. PATENT DOCUMENTS

| | | |
|---|---|---|
| 2011/0238172 A1 | 9/2011 | Akdis |
| 2014/0030122 A1 | 1/2014 | Ozaki et al. |
| 2015/0051436 A1 | 2/2015 | Spanier et al. |

OTHER PUBLICATIONS

European Search Report for corresponding European Patent Application No. 21182891.8 dated Nov. 8, 2021 (6 pages).
Office Action issued in corresponding Indian Patent Application No. 202037016554 dated Mar. 15, 2022 (6 pages).
Office Action from corresponding Chinese Patent Application No. 201880073236.4 dated Jun. 2, 2022 (17 pp.).
Office Action issued in corresponding Japanese Patent Application No. 2020-516571 dated Oct. 11, 2022, (11 pp.).

* cited by examiner

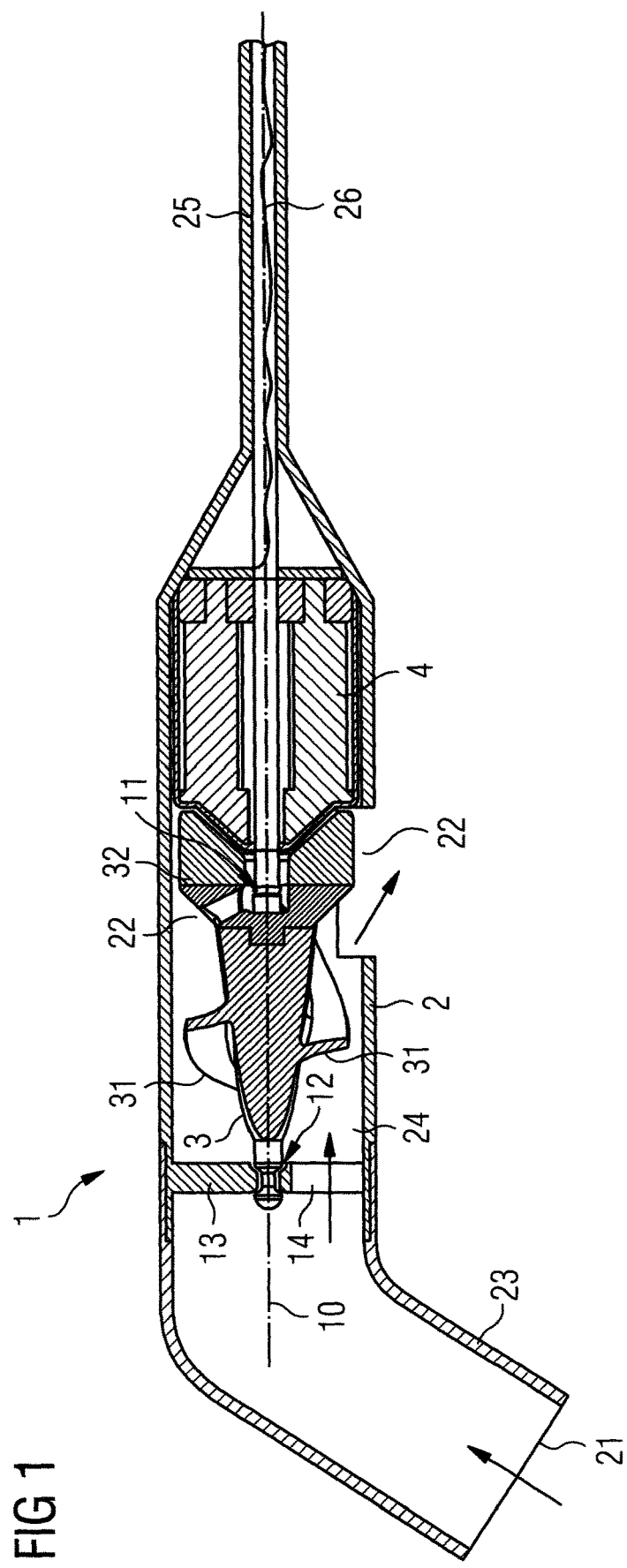

FIG 4
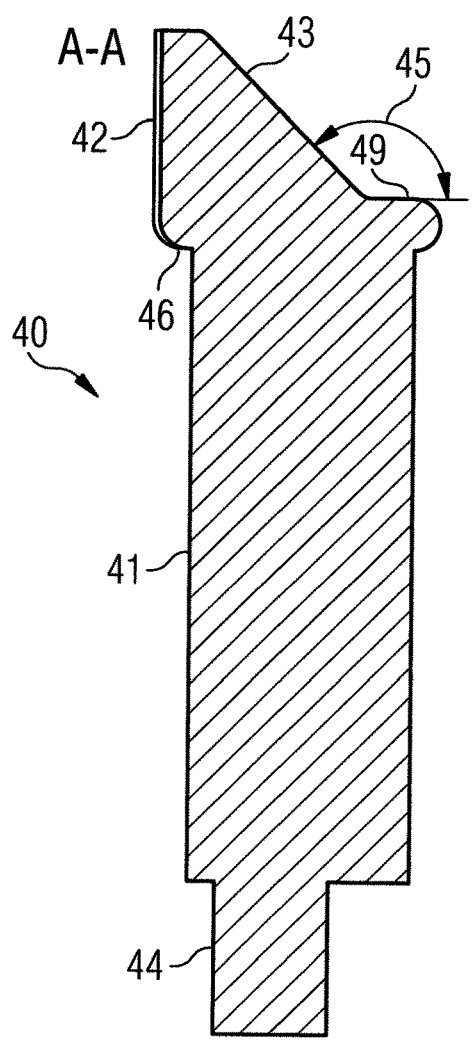
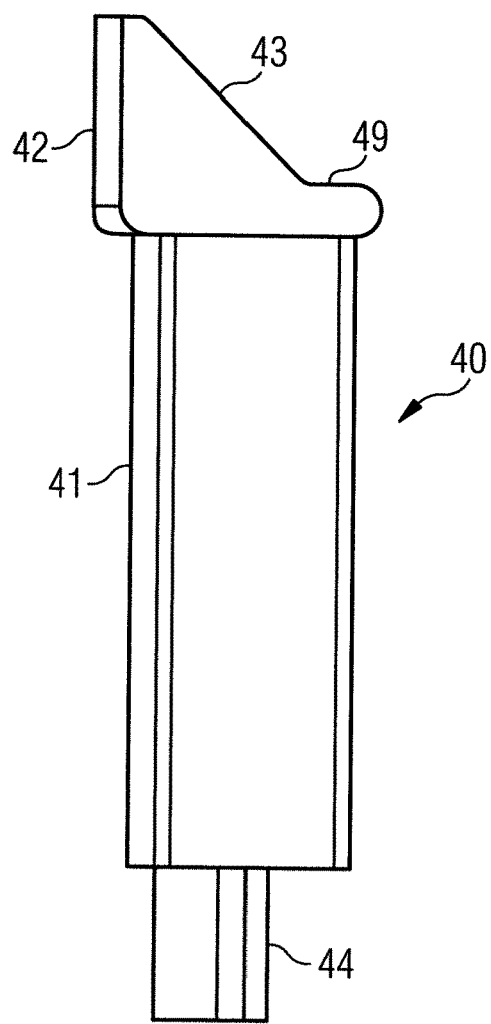
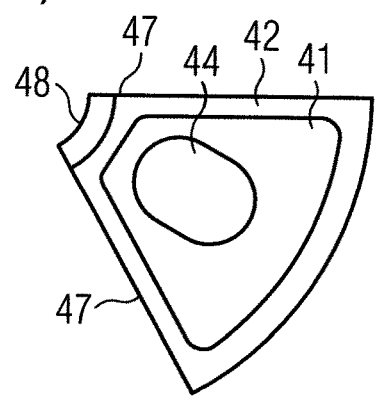
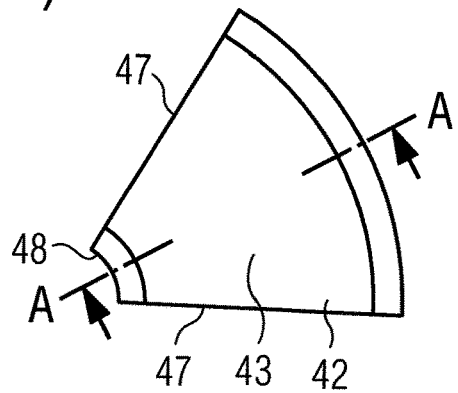

FIG 9
a)
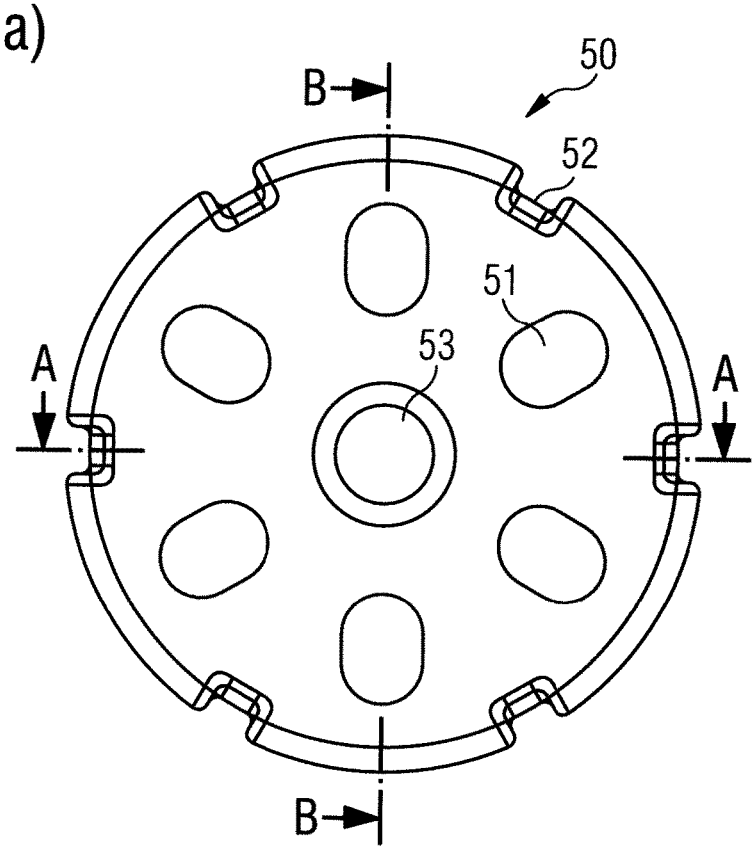
c)
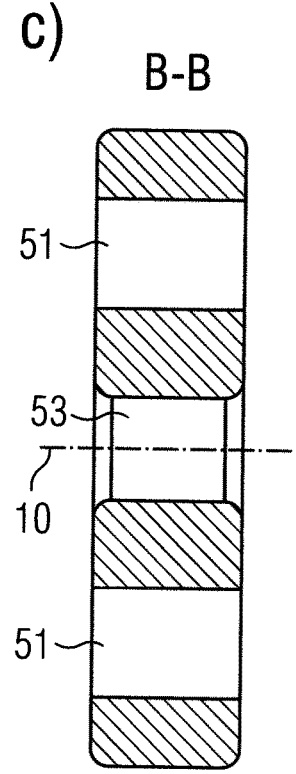
b)
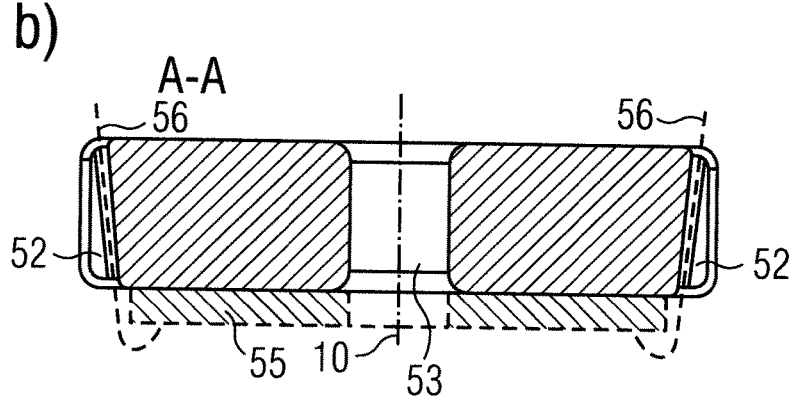

FIG 10
a)
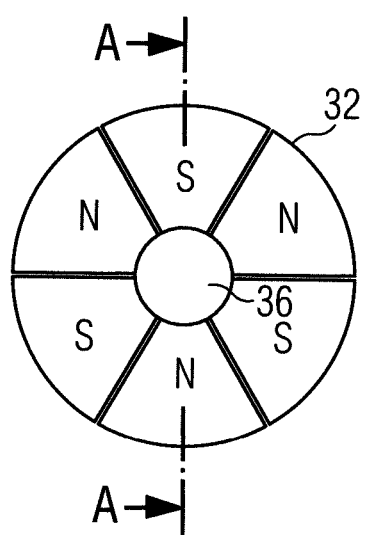
b)
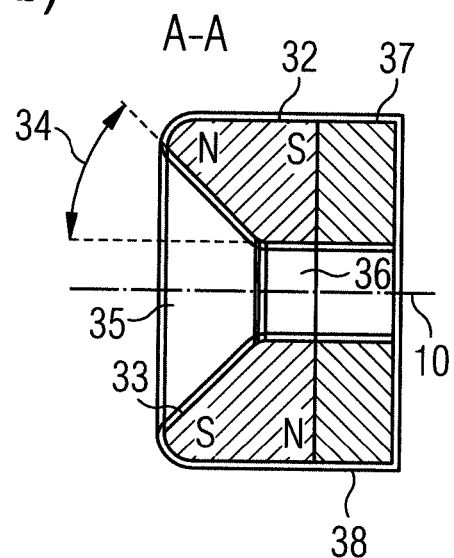
c)
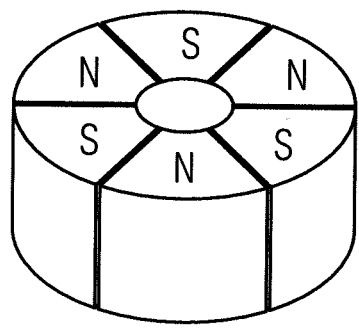

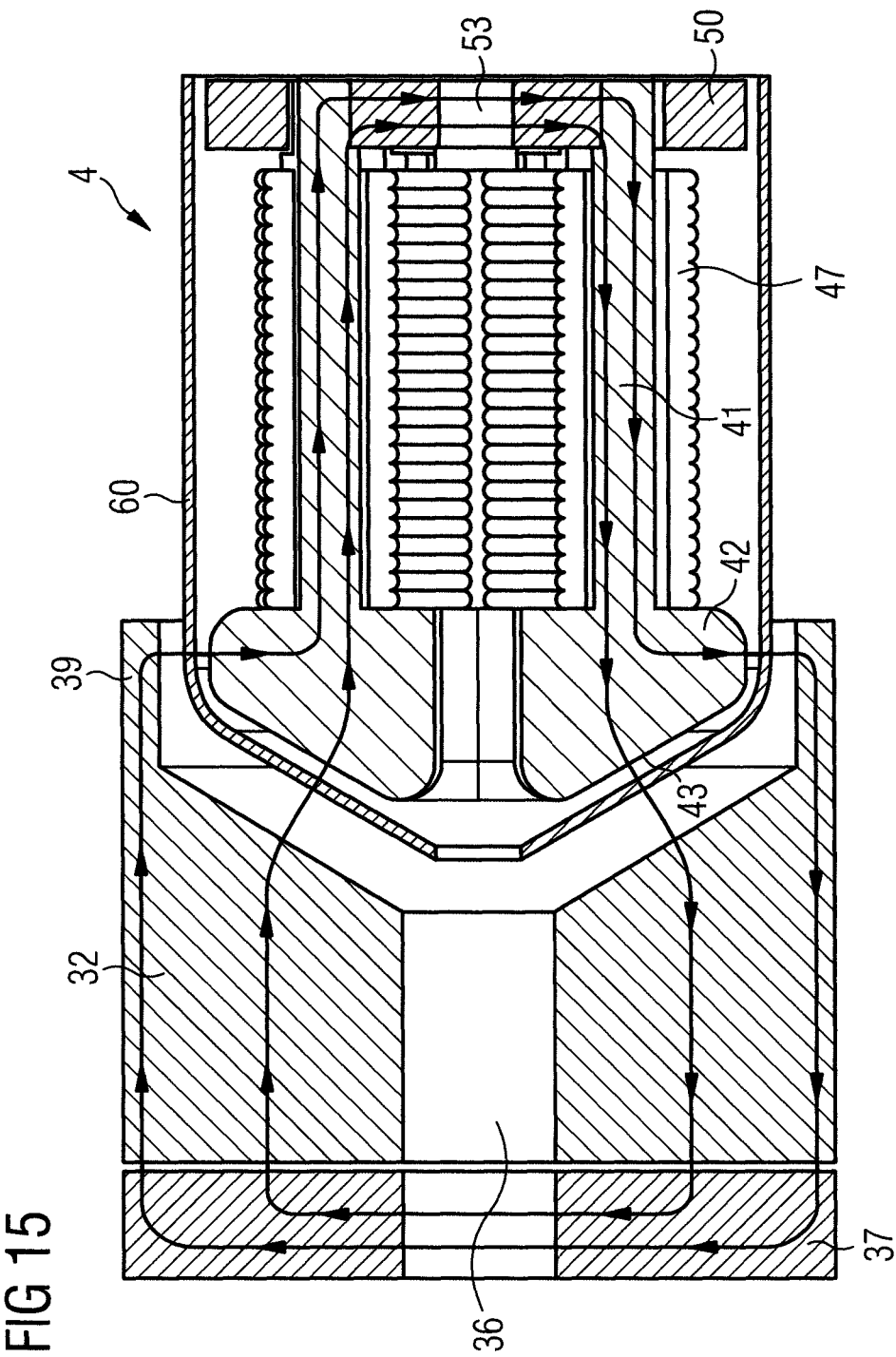

BLOOD PUMP

CROSS-REFERENCE TO RELATED APPLICATIONS

This application is a United States National Stage filing under 35 U.S.C. § 371 of International Application No. PCT/EP2018/074929, filed Sep. 14, 2018, which claims priority to European Patent Application No. 17191940.0, filed Sep. 19, 2017. The contents of each of each of the foregoing applications are hereby incorporated by reference in their entirety. International Application No. PCT/EP2018/074929 was published under PCT Article 21(2) in English.

BACKGROUND

This invention relates to a blood pump, in particular an intravascular blood pump for percutaneous insertion into a patient's blood vessel, to support a blood flow in a patient's blood vessel. The blood pump has an improved drive unit which allows for reduction of the outer diameter of the blood pump.

Blood pumps of different types are known, such as axial blood pumps, centrifugal (i.e. radial) blood pumps or mixed-type blood pumps, where the blood flow is caused by both axial and radial. Intravascular blood pumps are inserted into a patient's vessel such as the aorta forcesby means of a catheter. A blood pump typically comprises a pump casing having a blood flow inlet and a blood flow outlet connected by a passage. In order to cause a blood flow along the passage from the blood flow inlet to the blood flow outlet, an impeller or rotor is rotatably supported within the pump casing, with the impeller being provided with blades for conveying blood.

Blood pumps are typically driven by a drive unit, which can be an electric motor. For instance, US 2011/0238172 A1 discloses extracorporeal blood pumps having an impeller which may be magnetically coupled to an electric motor. The impeller comprises magnets which are disposed adjacent to magnets in the electric motor. Due to attracting forces between the magnets in the impeller and in the motor, rotation of the motor is transmitted to the impeller. In order to reduce the number of rotating parts, it is also known from US 2011/0238172 A1 to utilize a rotating magnetic field, with the drive unit having a plurality of static posts arranged about the axis of rotation, and each post carrying a wire coil winding and acting as a magnetic core. A control unit sequentially supplies a voltage to the coil windings to create the rotating magnetic field. In order to provide a sufficiently strong magnetic coupling, the magnetic forces have to be high enough, which can be achieved by a sufficiently high current supplied to the drive unit or by providing large magnets, which, however, leads to a large overall diameter of the blood pump. However, high energy consumption and heat generation may occur in such drive units.

SUMMARY OF THE INVENTION

It is therefore an object of the present invention to provide a blood pump, preferably an intravascular blood pump or transvalvular blood pump, having a magnetic coupling between the drive unit and the impeller, wherein the blood pump has a compact design, in particular a sufficiently small outer diameter to allow the blood pump to be inserted transvascularly, transvenously, transarterially or transvalvularly. It is further an object of the present invention to reduce heat and energy consumption of the blood pump, which is particularly useful for long-term applications in which the blood pump can be battery-powered to provide mobility for the patient.

This object is achieved according to the present invention by a blood pump having the features of independent claim 1. Preferred embodiments and further developments of the invention are specified in the claims dependent thereon.

According to the invention, the blood pump, which preferably is an intravascular blood pump and may be an axial blood pump or a diagonal blood pump, which pumps partly axially and partly radially, (the diameter of pure centrifugal blood pumps is usually too large for intravascular applications), comprises a drive unit for rotating the impeller. The drive unit comprises a plurality of posts, such as at least two, at least three, at least four, at least five or preferably six posts, that are arranged about the axis of rotation. Higher numbers of posts, such as eight, ten or twelve, may be possible. The number of posts is preferably even for a balanced control of the impeller, but it may also be odd, such as three or five. Each of the posts includes a shaft portion and a head portion, with the head portion pointing towards the impeller. In order to create a rotating magnetic field, a coil winding is disposed about the shaft portion of each of the posts, with the coil windings being sequentially controllable so as to create the rotating magnetic field. The impeller comprises at least one magnet, which is arranged to magnetically couple the impeller to the drive unit, i.e. to interact with the rotating magnetic field so as to cause rotation of the impeller.

A drive unit that creates a rotating electromagnetic field allows for simplification of the mechanics of the blood pump by reducing the number of moving parts compared to a common electric motor. This also reduces wear, because no contact bearing for an electric motor is necessary. The magnetic coupling between the drive unit and the impeller not only causes rotation of the impeller but also permits correct alignment of the impeller.

Each of the posts has a longitudinal axis, and the shaft portion of each of the posts extends along the longitudinal axis of the respective post. Preferably, the longitudinal axis of each post is parallel to the axis of rotation. The shaft portion of each of the posts comprises a soft magnetic material which is discontinuous in cross-section transverse, preferably perpendicular, to the longitudinal axis of the respective post. In other words, the soft magnetic material of the posts is discontinuous in cross-section transverse, preferably perpendicular, to a direction of magnetic flux caused by the respective coil winding in the shaft portion. By dividing or interrupting the soft magnetic material in cross section, eddy currents in the shaft portions of the posts can be reduced or avoided, such that heat generation and energy consumption can be reduced. Reducing energy consumption is particularly useful for long term applications of the blood pump, in which it is desirable that the blood pump is battery-powered to provide mobility for the patient. Also in long term applications, the blood pump may be operated without purge, which is only possible if heat generation is low.

"Discontinuous" in the sense of the present document means that the soft magnetic material as seen in any cross-section transverse to the longitudinal axis is interrupted, separated, intersected or the like by means of insulating material or other materials or gaps in order to form strictly separated areas of soft magnetic material or areas that are interrupted but connected at a different location.

Providing a discontinuous soft magnetic material in cross-sectional planes transverse to the direction of the magnetic flux reduces eddy currents and thus heat generation and energy consumption as explained above. In order not to substantially weaken the magnetic field compared to a continuous or full body (i.e. solid) soft magnetic material, the total amount of soft magnetic material is to be maximized while minimizing the continuous areas of soft magnetic material. This can be achieved for example by providing the soft magnetic material in the form of a plurality of sheets of soft magnetic material, such as electric steel. In particular, the sheets may form a stack of sheets. The sheets are preferably electrically insulated from each other, e.g. by providing adhesive, lacquer, baking enamel or the like between adjacent ones of the sheets. Such arrangement can be denoted as "slotted". Compared to a full body soft magnetic material, the amount of soft magnetic material is recued only little and the amount of insulating material is kept small, such that the magnetic field caused by a slotted post is substantially the same as the magnetic field caused by a solid post. In other words, while heat generation and energy consumption can be reduced significantly, the loss in magnetic field caused by the insulating material is insignificant.

The sheets preferably extend substantially parallel to the longitudinal axis of the respective post. In other words, the sheets may extend substantially parallel to the direction of the magnetic flux, such that the shaft portions are discontinuous in cross-section transverse or perpendicular to the direction of the magnetic flux. It will be appreciated that the sheets may extend at an angle relative to the longitudinal axis of the respective post as long as the soft magnetic material is discontinuous in cross-section transverse to the longitudinal axis. The sheets preferably have a thickness in the range of about 25 µm to about 350 µm, more preferably about 50 µm to about 200 µm, for instance 100 µm.

It is generally known to provide slotted soft magnetic material, such as electrical steel, in electric motors to avoid or reduce eddy currents. However, this technology has been applied for large devices in which the sheets usually have a thickness in the range of about 500 µm or higher. In small applications, such as the blood pump of the present invention, in which one of the posts, more specifically the respective shaft portion, usually has a diameter in said order of magnitude, and in which the power input is relatively low (e.g. up to 20 watts (W)), eddy currents and the associated problems were not expected. Surprisingly, despite the small diameter of the shaft portions, eddy currents and thus heat generation and energy consumption can be reduced by providing a slotted shaft portion. This is advantageous for operation of the blood pump, which may be operated at a high speed of up to 50,000 rpm (revolutions per minute).

It will be appreciated that other arrangements than the aforementioned slotted arrangement to provide a discontinuous soft magnetic material in the shaft portions of the posts may be possible. For instance, instead of a plurality of sheets, a plurality of wires, fibers, posts or other elongate elements can be provided to form each of the posts of the drive unit. The wires or the like may be provided in the form of a bundle with the wires being electrically insulated from each other, e.g. by means of a coating surrounding each wire or an insulating matrix in which the wires are embedded, and may have various cross-sectional shapes, such as circular, round, rectangular, square, polygonal etc. Likewise, particles of a soft magnetic material, wire wool or other sponge-like or porous structures of soft magnetic material can be provided, in which the space between the areas of soft magnetic material comprises an electrically insulating material, such as an adhesive, lacquer, polymer matrix or the like.

A porous and, thus, discontinuous structure of soft magnetic material may also be formed by a sintered material or pressed material. In such structure, an additional insulating material may be omitted because insulating layers may be formed automatically by oxide layers resulting from oxidation of the soft magnetic material by exposure to air.

While the sheets or other structures of soft magnetic material may be formed uniformly, i.e. the sheets within one of the posts or all posts may have the same thickness or wires may have the same diameter, a non-uniform arrangement can be provided. For instance, the sheets may have a varying thickness or the wires may have a varying diameter. More specifically, in particular with regards to a stack of sheets, one or more central sheets may have a larger thickness, while adjacent sheets towards the ends of the stack may have a smaller thickness, i.e. the thickness of the sheets decreases from the center towards the ends of the stack, i.e. towards the outermost sheets of the stack. Similarly, one or more central wires in a bundle of wires may have a larger diameter, while wires at the edge of the shaft portion of the post may have a smaller diameter, i.e. the diameter of the wires may decrease from the center towards the edges of the bundle, i.e. towards the outermost wires of the bundle. Providing a larger continuous area of soft magnetic material in the center of the shaft portion with respect to a cross-section transverse to its longitudinal axis, i.e. relatively thick sheets or wires in the center, may be advantageous because this may enhance the magnetic flux through the center along the longitudinal axis of each post, and eddy currents in the center are less relevant than eddy currents at the sides of the posts. In other words, such arrangement may be advantageous because eddy currents in the side regions of the shaft portions are more critical and can be reduced by thin sheets or wires in the side regions.

In one embodiment, the head portion of each of the posts may comprise a soft magnetic material that is discontinuous in cross-section perpendicular to the longitudinal axis of the respective post. Substantially all features and explanations as set forth above with respect to the discontinuous material of the shaft portions are valid for the head portions. For instance, like the shaft portions, the head portions may be slotted, and the sheets of the head portions are preferably electrically insulated from each other. Since the magnetic flux in the head portions is substantially parallel to the axis of rotation or the longitudinal axis of the respective post, especially if the head portions do not have inclined surfaces as will be described below, the soft magnetic material of the head portions may be provided in the form of a plurality of sheets that extend parallel to the longitudinal axis of the respective post, or to the axis or rotation. In other words, the sheets in the head portions may extend substantially in the same direction as the sheets of the shaft portions. As explained in the aforementioned, eddy currents and thereby heat generation and power consumption can be reduced. However, since eddy currents in the head portions are usually low, the effect of a discontinuous material compared to a solid material is not as significant as in the shaft portions. Thus, the head portions may be alternatively formed of continuous, i.e. solid, soft magnetic material.

The drive unit may further comprise a back plate which may engage ends of the shaft portions of the plurality of posts that are opposite to the head portions. In one embodiment, the back plate may comprise a plurality of apertures arranged about the axis of rotation for receiving said ends of the shaft portions, preferably at a regular angular distance. However, it will be appreciated that the post can be attached, connected or secured to the back plate by other means, either permanently or releasably. The back plate particularly serves for closing the magnetic flux circuit to facilitate and increase the magnetic flux generation and improve the coupling capability. Since the magnetic flux is increased by the back plate, the overall diameter of the blood pump can be reduced, which is particularly advantageous for intravascular blood pumps. The arrangement including the posts with the back plate further allows for high frequencies of the blood pump, i.e. the blood pump can operate at a high speed, e.g. up to about 50,000 rpm. In addition, as the back plate engages the posts, the back plate provides structural stability for the post assembly.

Like the shaft portions and possibly the head portions of the posts, the back plate may comprise a discontinuous soft magnetic material. Since the magnetic flux in the back plate is substantially transverse or perpendicular to the axis of rotation, the soft magnetic material of the back plate is preferably discontinuous in cross-section parallel to the axis of rotation. Apart from that, substantially all features and explanations mentioned above with respect to the discontinuous material of the shaft portions are valid also for the back plate. For instance, like the shaft portions, the back plate may be slotted, i.e. may be formed of a plurality of stacked sheets, and the sheets of the back plate are preferably electrically insulated from each other. The sheets of the back plate may extend substantially perpendicularly to the sheets of the shaft portions and substantially parallel to the sheets of the head portions. As explained in the aforementioned, eddy currents and thereby heat generation and power consumption can be reduced. However, the back plate may be alternatively formed of continuous, i.e. solid, soft magnetic material.

The back plate, like the posts, is preferably made of a soft magnetic material, such as electrical steel (magnetic steel) or other material suitable for closing the magnetic flux circuit, preferably cobalt steel. The diameter of the back plate may be about 3 mm to 9 mm, such as 5 mm or 6 mm to 7 mm. The thickness of the back plate may be about 0.5 mm to about 2.5 mm, such as 1.5 mm. The outer diameter of the blood pump may be from about 4 mm to about 10 mm, preferably about 6 mm. The outer diameter of the arrangement of the plurality of posts, in particular the largest outer diameter of the arrangement of the plurality of posts which is measured at the head portions of the posts may be about 3 mm to 8 mm, such as 4 mm to 6 mm, preferably 5 mm.

As stated above, the posts are made of a soft magnetic material such as electrical steel (magnetic steel). The posts and the back plates may be made of the same material. Preferably, the drive unit, including the posts and the back plate, is made of cobalt steel. The use of the cobalt steel contributes to reducing the pump size, in particular the diameter. With the highest magnetic permeability and highest magnetic saturation flux density among all magnetic steels, cobalt steel produces the most magnetic flux for the same amount of material used.

The dimensions of the posts, in particular length and cross-sectional area, may vary and depend on various factors. In contrast to the dimensions of the blood pump, e.g. the outer diameter, which depend on the application of the blood pump, the dimensions of the posts are determined by electromagnetic properties, which are adjusted to achieve a desired performance of the drive unit. One of the factors is the flux density to be achieved through the smallest cross-sectional area of the posts. The smaller the cross-sectional area, the higher is the necessary current to achieve the desired magnetic flux. A higher current, however, generates more heat in the wire of the coil due to electrical resistance. That means, although "thin" posts are preferred to reduce the overall size, this would require high current and, thus, result in undesired heat. The heat generated in the wire also depends on the length and diameter of the wire used for the coil windings. A short wire length and a large wire diameter are preferred in order to minimize the winding loss (referred to as "copper loss" or "copper power loss" if copper wires are used, which is usually the case).

In other words, if the wire diameter is small, more heat is generated compared to a thicker wire at the same current, a preferred wire diameter being e.g. 0.05 mm to 0.2 mm, such as 0.1 mm. Further factors influencing the post dimensions and the performance of the drive unit are the number of windings of the coil and the outer diameter of the windings, i.e. the post including the windings. A large number of windings may be arranged in more than one layer around each post, for instance, two or three layers may be provided. However, the higher the number of layers, the more heat will be generated due to the increased length of the wire in the outer layers having a larger winding diameter. The increased length of the wire may generate more heat due to the higher resistance of a long wire compared to a shorter one. Thus, a single layer of windings with a small winding diameter would be preferred.

A typical number of windings, which in turn depends on the length of the post, may be about 50 to about 150, e.g. 56 or 132. Independent of the number of windings, the coil windings are made of an electrically conductive material, in particular metal, such as copper or silver. Silver may be preferred to copper because silver has an electrical resistance which is about 5% less than the electrical resistance of copper.

In one embodiment, the impeller may also comprise a yoke or back plate that is attached to the at least one magnet of the impeller, preferably at a side of the impeller facing away from the drive unit, e.g. between the magnet and blades of the impeller. Like the back plate that is attached to the ends of the shafts of the posts, the yoke or back plate of the impeller serves for closing the magnetic flux circuit to increase the magnetic flux generation and enhance the coupling capability. It may be made of magnetic steel, preferably cobalt steel.

In order to increase the density of the magnetic coupling between the drive unit and the magnets of the impeller, it may be advantageous to activate several posts simultaneously, where "activate" means to supply electric power to the respective coil winding in order to create a respective pole magnet. For example, more than half of the posts may be activated at the same time, such as four of six posts, depending on the number of posts and number of magnets in the impeller. Preferably, the arrangement of activated and inactivated posts is rotationally symmetrical and the posts are controlled preferably in pairs of diametrically opposing posts.

It may be further advantageous for the efficiency and performance of the drive unit if the posts are magnetically insulated against each other. Thus, a magnetically insulating material may be disposed between the head portions of adjacent posts so as to separate the posts from each other and keep the respective magnetic field within the respective post. The magnetically insulating material may be a magnetic material, the magnetic field of which keeps the electromagnetic field caused by the coil windings within the respective post. At least, an air gap or other insulating, i.e. electrically non-conductive, material may be provided between the head portions of the posts to avoid a short-circuit between the posts.

In one embodiment, the head portion of at least one of the posts, preferably of each of the posts, has a top surface that is inclined at an angle relative to a plane perpendicular to the axis of rotation. A distance between the axis of rotation and a center in a radial direction of said inclined surface may be less than or equal to a distance between the axis of rotation and a center in a radial direction of a cross-sectional area of the shaft portion of the respective post. The center in a radial direction of a surface or area is the center between a radially innermost point and a radially outermost point of the surface or area. In other words, the inclined top surface of the head portion, which is the surface facing the impeller, may extend obliquely or may be inclined at an angle relative to the axis of rotation, and half or more of the inclined surface may be located radially inwards relative to the center of the shaft portion. This enables the outer diameter of the drive unit and, thus, of the blood pump, to be kept at a minimum that is necessary for magnetically coupling the drive unit to the impeller. This reduced diameter design is particularly advantageous for intravascular blood pumps that are located within a patient's blood vessel during pump operation and can be deployed by means of a catheter. In addition, the inclined coupling surface provides for radial centering of the impeller. The aforementioned angle is preferably 45°, but may be between about 0° and about 90°, preferably between about 30° and about 60°, more preferably between about 40° to about 50°, with respect to a plane perpendicular to the axis of rotation. The inclined surfaces of the posts preferably face radially outwards, i.e. they form a convex shape. Alternatively, the inclined surfaces may face radially inwards to form a concave shape.

In another embodiment, the top surfaces of the head portions of the posts may be perpendicular to the axis of rotation. In other words, the top surfaces of the head portions may have no inclination compared to the aforementioned embodiment, such that the head portions do not form a conical shape but form a flat plane. Accordingly, the magnets in this embodiment are not inclined but form a flat plane that is parallel to the plane formed by the top surfaces of the head portions.

All of the posts preferably are identical such that the drive unit is symmetrical with respect to the axis of rotation. It will be appreciated, however, that the posts do not have to be exactly identical as long as they are compatible for forming the drive unit according to the invention. However, it is preferable for shaft portions to have the same length and the inclined surfaces of the head portions to have the same angle of inclination. Different posts may be irregularly or regularly arranged to form the drive unit, such as in an alternating manner.

The top surface of the head portion, preferably of each of the head portions, whether inclined or not as explained above, may be radially aligned with or be located radially inwards or outwards with respect to a radially outermost surface of the coil winding of the respective post. The top surface preferably extends radially inwards beyond the respective shaft portion towards the axis of rotation so as to maximize the surface area of the magnetic bearing, while minimizing the outer diameter of the drive unit. For instance, in an axial projection, i.e. as seen in a top view in an axial direction, the top surface of the head portion may be located within the coil winding or may be at least aligned with the shaft or coil winding in an axial direction. In another embodiment, the head portion may extend beyond the outer circumference of the coil winding in a radial and/or circumferential direction. The head portion may have a larger cross-sectional dimension than the respective shaft portion in a plane perpendicular to the axis of rotation, with the respective coil winding preferably not extending beyond the head portion at least in a radial direction. In other words, the head portion may form a shoulder, which can act as an axial stop for the coil winding as well as a radial limitation.

In case the top surfaces of the head portions are oblique or inclined, at least one of the head portions, preferably all head portions, may be substantially triangular or trapezoidal in cross-section along a plane including the axis of rotation. In the assembled state, the oblique or inclined surfaces of the head portions may together form a conical surface or substantially conical surface, e.g. a surface having facets but forming approximately a conical surface. Generally, the shape of the formed surface can be convex. Illustratively speaking, the head portions may be put together like pie slices to form a circular arrangement having a conical top surface. The at least one magnet of the impeller may have or may form a conical or substantially conical recess substantially corresponding in size and shape to the conical surface formed by the head portions of the posts. Generally, the magnet may form a concave surface facing the convex surface formed by the posts to improve the magnetic coupling. In another embodiment, the arrangement of concave and convex surfaces may be vice versa, i.e. the head portions of the posts may form a conical recess while the magnet forms a convex conical surface.

The respective convex and concave surfaces of the drive unit and the impeller respectively may form a gap such that the distance between the surfaces is constant. Preferably, however, the gap distance is not constant but is chosen such that the cross-sectional area of the gap, viewed in a circumferential direction, is constant in a radial direction. In the latter case the distance between the surfaces increases towards the axis of rotation. Combinations may also be envisioned. The shape and dimension of the gap between the impeller and the drive unit may contribute to hydrodynamic bearing capabilities. Similarly, such gap is provided if the top surfaces of the head portions are not inclined.

The magnet of the impeller may be formed as a single piece having the conical or substantially conical recess that corresponds to the shape of the head portions of the posts, including a gap with varying distance as explained above. It will be appreciated, however, that there may be provided a plurality of magnets, such as two or more, e.g. four, preferably six magnets, or even eight, ten or twelve magnets, that are arranged in the impeller about the axis of rotation and form the conical recess. Providing a plurality of magnets, preferably an even number, more preferably a number corresponding to the number of posts, is advantageous because the magnets can be arranged with alternating north/south orientations of the magnetic field without dead zones. If the magnet is provided as a single piece, dead zones may be created at the transitions between differently oriented magnetic fields. It will be appreciated that the aforementioned structure may also apply if the magnet or magnets and the top surfaces of the head portions are not inclined but lie in planes perpendicular to the axis of rotation.

If the impeller includes a plurality of magnets, the magnets may be arranged with substantially no gaps between the individual magnets in order to increase the amount of magnetic material. However, it has been found that the efficiency of the magnetic coupling does not decrease if the magnets are separated by gaps, in particular radially extending gaps. This is because of the characteristics of the magnetic field and the gap between the drive unit and the impeller. If the magnets in the impeller are close to each other, the innermost magnetic field lines, which extend in an arch from one magnet (north) to an adjacent magnet (south), do not extend beyond the gap between the drive unit and the impeller and, thus, do not reach the drive unit, i.e. they do not contribute to the drive of the impeller. Therefore, there is no loss in efficiency if a gap is provided between the magnets in the impeller. The size of gap between the magnets in the impeller that can be provided without loss of efficiency of the drive is dependent on the size of the gap between the impeller and the drive unit as a skilled person can calculate. The gaps between the impeller magnets can then be used e.g. as wash out channels.

Generally speaking and regardless of whether the head portions form a conical surface, the magnet of the impeller may have a surface that faces the head portions of the posts and is inclined at an angle substantially corresponding to the angle of the inclined surfaces of the head portions. For instance, the arrangement may be the converse of the aforementioned arrangement, that is to say, the head portions of the posts may form a concave surface, such as a conical recess, and the magnet of the impeller may form a convex surface, such as a conical surface. This also applies if the surfaces are not inclined, i.e. if the aforementioned angle is 90 degrees with respect to the axis of rotation.

Regardless of the inclination of the respective surfaces, the magnet or magnets of the impeller may be radially aligned with the head portions of the posts. However, in some embodiments, the magnet or magnets of the impeller may be radially offset with respect to the head portions of the posts, such as radially inwards or radially outwards. This radial offset may improve stabilizing and radial centering of the impeller because the magnetic forces between the impeller and the drive unit have a radial component, whereas the magnetic forces are directed merely substantially axially if the magnets are radially aligned with the head portion of the posts.

In one embodiment, the impeller may extend at least partially about the drive unit, in particular the head portions of the posts. In other words, the impeller may have an extension that overlaps the drive unit in a circumferential direction. That means the magnetic coupling takes place not only in the region of the inclined surfaces of the head portions of the posts but also on radially outer side surfaces thereof. The impeller may have an increased diameter, in particular a larger diameter than the drive unit, such that the impeller can extend about the area of the head portions of the posts. The impeller may, thus, have a recess that has a conical portion as described above and a cylindrical portion. The magnetic coupling can be improved by this design of the impeller because the impeller and the drive unit are coupled in a radial direction as well, where the magnetic field lines extend in a radial direction. In this area, a high torque can be created to drive the impeller due to the largest diameter.

In one embodiment, the intravascular blood pump may further comprise a housing surrounding the drive unit, with the housing preferably corresponding in size and shape to an outer contour of the plurality of posts. In particular, the housing may have a conical axial end surface corresponding to the shape of the surface formed by the inclined surfaces of the posts' head portions. The opposite end may be open and may engage the back plate to close the housing. The housing serves as a protection for the post assembly, particularly as a protection against blood contact, which is particularly useful for the coil windings. Preferably, the housing is disposed inside the pump casing. Regardless of the presence of such housing, the drive unit preferably is arranged inside the pump casing. The housing is preferably made of a non-magnetic and non-conductive (i.e. electrically insulating) material and provides good heat transfer. The material of the housing may be e.g. aluminum.

The coil windings may be embedded in a thermally conductive matrix, which is electrically non-conductive (i.e. electrically insulting). The matrix protects the coil windings and transfers heat produced by the coil windings. The material of the thermally conductive matrix maybe a plastics material with additives in order to increase the thermally conductive characteristics. For instance, the matrix may comprise an epoxy resin with aluminum additives. The matrix may be formed by molding the material around and between the coil windings and subsequently curing the material.

The drive unit may have a central opening that extends along the axis of rotation. The central opening may be formed by the head portions of the posts and may be configured for receiving an elongate pin or shaft, with an axial end surface of the pin being sized and dimensioned to form a bearing surface for the impeller. This arrangement allows for a compact design of the blood pump because the space between the posts is used for the pin. The other end of the pin may be supported by the pump casing. The central opening may also be provided for insertion of a guide wire or the like or may form a fluid path. In another embodiment in which the blood pump does not have a shaft that extends all the way through the drive unit, such central opening can be omitted.

In order to enhance a wash-out flow through the gap between the impeller and the drive unit, a secondary set of blades may be provided in the impeller. In particular, secondary blades may be provided on the side of the magnet or magnets that faces the drive unit, i.e. in the gap between the impeller and the drive unit. The wash-out flow may additionally or alternatively be increased by channels that are recessed in the surface of the magnet that faces the drive unit. The channels may extend e.g. radially or helically.

In one embodiment, one or more hydrodynamic bearings may be provided to support the impeller. For instance, the aforementioned secondary blades and the channels may form a hydrodynamic bearing or at least support hydrodynamic bearing capabilities as mentioned above with respect to the size and shape of the gap between the impeller and the drive unit. Conversely, the surface of the drive unit that faces the impeller, i.e. in particular the end surface of the housing that encloses the drive unit, may be adapted to form a hydrodynamic bearing. The hydrodynamic bearing may be axial or radial or both axial and radial. In particular because of the conical shape of the interface between the impeller and the drive unit, a hydrodynamic bearing in both radial and axial directions can be formed. A radial hydrodynamic bearing may also be formed between an outer surface of the impeller and an inner surface of the pump casing. In particular, a gap may be formed between the impeller and the pump casing, where an amount of blood sufficient for the hydrodynamic bearing flows through the gap and exits the pump casing through an additional blood flow outlet. The main blood flow exits the pump casing through the blood flow outlet and does not flow through the gap. Hydrodynamic bearings, which are contactless bearings, may support the function of the drive unit by reducing frictional forces.

BRIEF DESCRIPTION OF THE DRAWINGS

The foregoing summary, as well as the following detailed description of preferred embodiments, will be better understood when read in conjunction with the appended drawings. For the purpose of illustrating the present disclosure, reference is made to the drawings. The scope of the disclosure is not limited, however, to the specific embodiments disclosed in the drawings. In the drawings:

FIG. 1 shows a cross-sectional view of a blood pump according to the invention.

FIGS. 4a-4d show different views of another embodiment of a post.

FIGS. 9a-9c show different views of a back plate.

FIGS. 10a-10c show different views of the magnets of the impeller.

FIG. 15 shows a cross-sectional view of a drive unit and impeller magnets according to another embodiment.

DETAILED DESCRIPTION

Figure 2A:
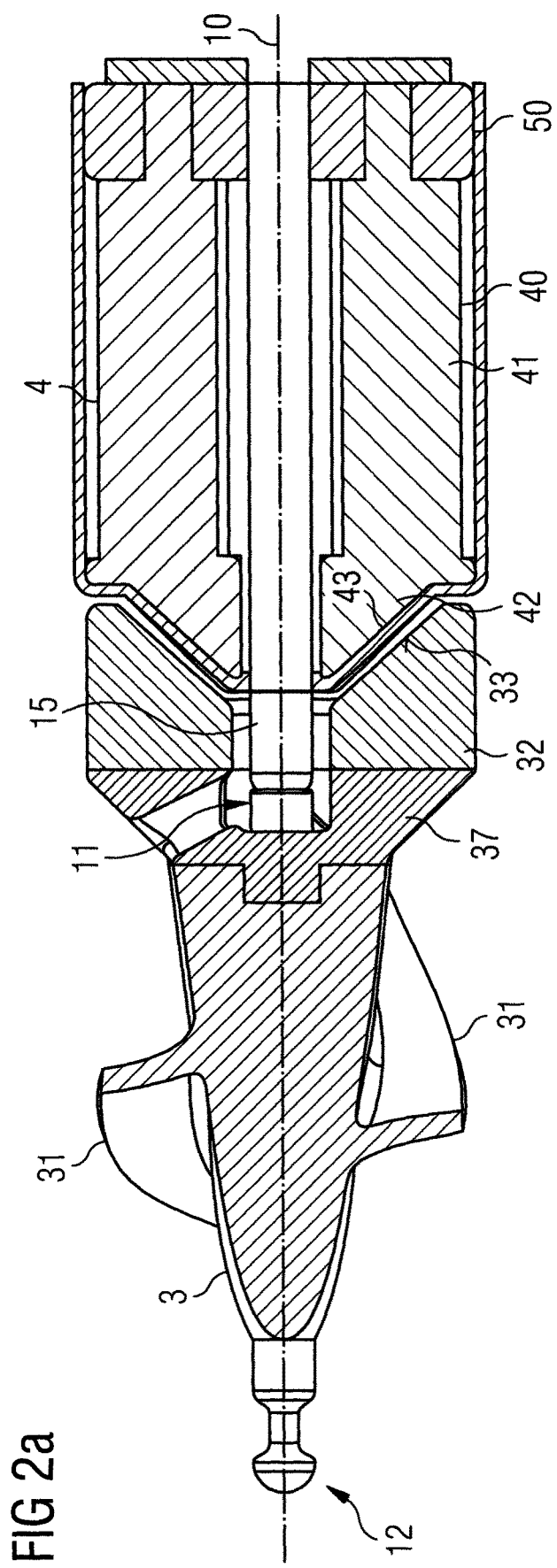
FIG. 2a shows an enlarged detail of the blood pump of FIG. 1.

Referring to FIG. 1, a cross-sectional view of a blood pump 1 is illustrated. FIG. 2 shows an enlarged view of the interior of the blood pump 1. The blood pump 1 comprises a pump casing 2 with a blood flow inlet 21 and a blood flow outlet 22. The blood pump 1 is designed as an intravascular pump, also called a catheter pump, and is deployed into a patient's blood vessel by means of a catheter 25. The blood flow inlet 21 is at the end of a flexible cannula 23 which may be placed through a heart valve, such as the aortic valve, during use. The blood flow outlet 22 is located in a side surface of the pump casing 2 and may be placed in a heart vessel, such as the aorta. The blood pump 1 is connected to the catheter 25, with an electric line 26 extending through the catheter 25 for supplying the blood pump 1 with electric power in order to drive the pump 1 by means of a drive unit 4, as explained in more detail below.

If the blood pump 1 is intended to be used in long term applications, i.e. in situations in which the blood pump 1 is implanted into the patient for several weeks or even months, electric power is preferably supplied by means of a battery. This allows a patient to be mobile because the patient is not connected to a base station by means of cables. The battery can be carried by the patient and may supply electric energy to the blood pump 1, e.g. wirelessly.

The blood is conveyed along a passage 24 connecting the blood flow inlet 21 and the blood flow outlet 22 (blood flow indicated by arrows). An impeller 3 is provided for conveying blood along the passage 24 and is mounted to be rotatable about an axis of rotation 10 within the pump casing 2 by means of a first bearing 11 and a second bearing 12. The axis of rotation 10 is preferably the longitudinal axis of the impeller 3. Both bearings 11, 12 are contact-type bearings in this embodiment. At least one of the bearings 11, 12 could be a non-contact-type bearing, however, such as a magnetic or hydrodynamic bearing. The first bearing 11 is a pivot bearing having spherical bearing surfaces that allow for rotational movement as well as pivoting movement to some degree. A pin 15 is provided, forming one of the bearing surfaces. The second bearing 12 is disposed in a supporting member 13 to stabilize the rotation of the impeller 3, the supporting member 13 having at least one opening 14 for the blood flow. Blades 31 are provided on the impeller 3 for conveying blood once the impeller 3 rotates. Rotation of the impeller 3 is caused by a drive unit 4 magnetically coupled to a magnet 32 at an end portion of the impeller 3. The illustrated blood pump 1 is a mixed-type blood pump, with the major direction of flow being axial. It will be appreciated that the blood pump 1 could also be a purely axial blood pump, depending on the arrangement of the impeller 3, in particular the blades 31.

FIG. 2a illustrates in more detail the interior of the blood pump 1, in particular the impeller 3 and the drive unit 4. The drive unit 4 comprises a plurality of posts 40, such as six posts 40, only two of which are visible in the cross-sectional view of FIG. 2. The posts 40 have a shaft portion 41 and a head portion 42. The head portion 42 is disposed adjacent to the impeller 3 in order to magnetically couple the drive unit 4 to the impeller 3. For this purpose, the impeller 3 has a magnet 32, which is formed as a multiple piece magnet in this embodiment as described in more detail with reference to FIGS. 10a-c. The magnet 32 is disposed at the end of the impeller 3 facing the drive unit 4. The posts 40 are sequentially controlled by a control unit (not shown) in order to create a rotating magnetic field for driving the blood pump 1. The magnet 32 is arranged to interact with the rotating magnetic field so as to cause rotation of the impeller 3 about the axis of rotation 10. Coil windings are arranged about the shaft portions 41 of the posts 40, as described in more detail below with reference to FIG. 7. The posts 40 are arranged parallel to the axis of rotation 10, more specifically, a longitudinal axis of each of the posts 40 is parallel to the axis of rotation 10.

In order to close the magnetic flux path, a back plate 50 is located at the end of the shaft portions 41 opposite the head portions 42. The posts 40 act as a magnetic core and are made of a suitable material, in particular a soft magnetic material, such as steel or a suitable alloy, in particular cobalt steel. Likewise, the back plate 50 is made of a suitable soft magnetic material, such as cobalt steel. The back plate 50 enhances the magnetic flux, which allows for reduction of the overall diameter of the blood pump 1, which is important for intravascular blood pumps. For the same purpose, a yoke 37, i.e. an additional back plate, is provided in the impeller 3 at a side of the magnet 32 facing away from the drive unit 4. The yoke 37 in this embodiment has a conical shape in order to guide the blood flow along the impeller 3. The yoke 37 may be made of cobalt steel, too. One or more wash-out channels that extend towards the central bearing may be formed in the yoke 37 or the magnet 32.

Figure 2B:
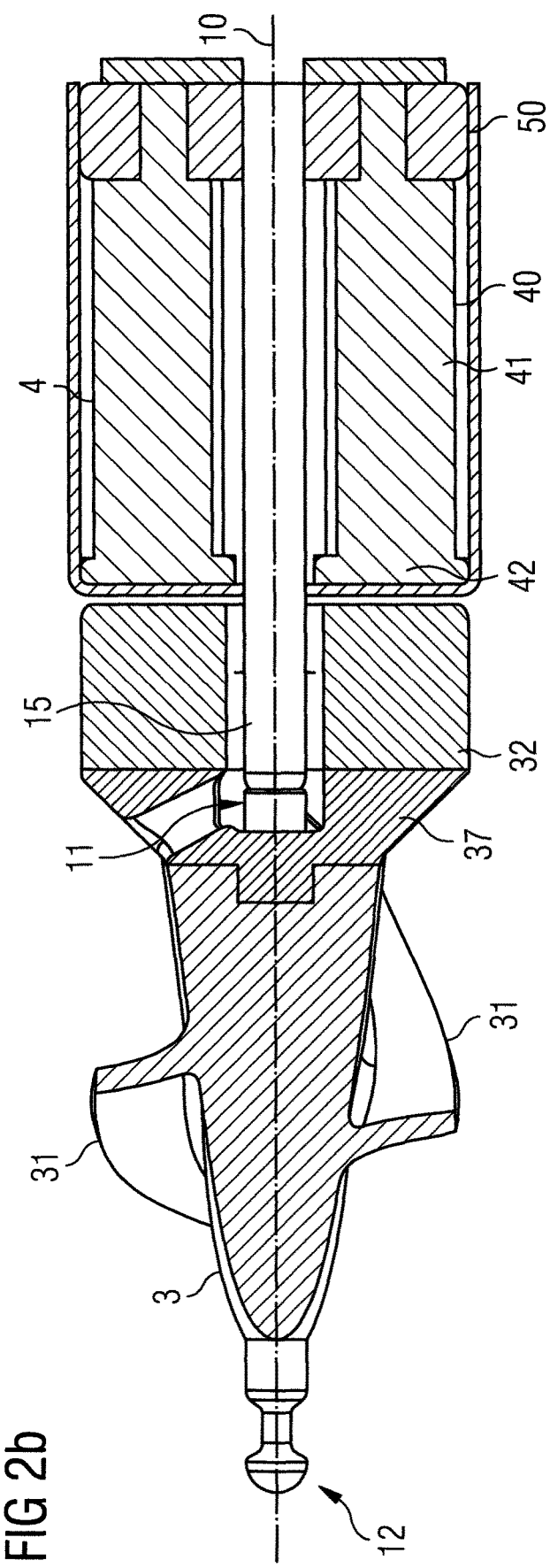
FIG. 2b shows the same view as FIG. 2a according to an alternative embodiment.

FIG. 2b illustrates an alternative embodiment which is substantially similar to the embodiment of FIG. 1 and FIG. 2a with the exception that top surfaces of the head portions 42 facing the magnet 32 are not inclined but extend in a plane perpendicular to the axis of rotation. Accordingly, the magnet 32 does not have inclined surfaces but forms a substantially cylindrical shape.

Figure 3:
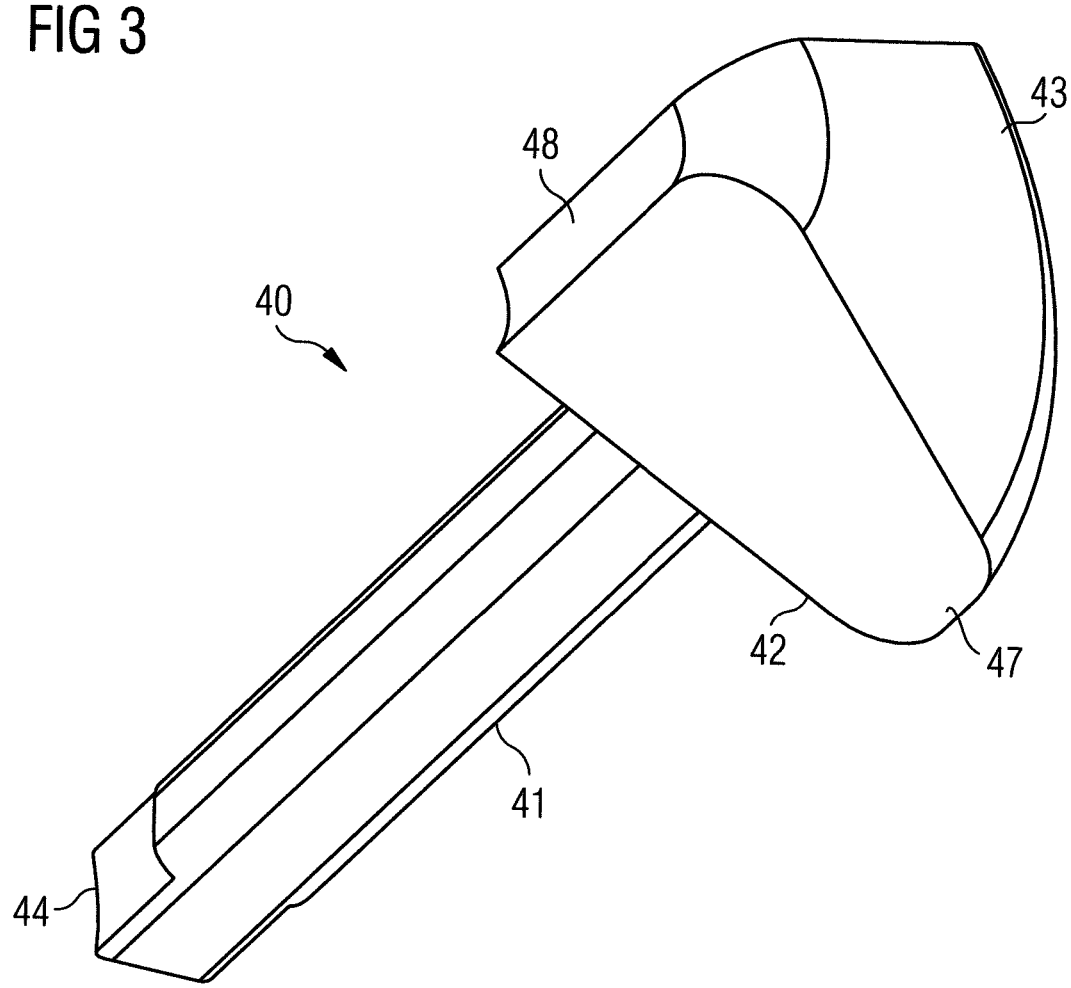
FIG. 3 shows a perspective view of a post of a drive unit.

Details of the drive unit 4 are shown in FIGS. 3 to 9, while FIG. 10 illustrates the magnet 32 of the impeller 3. Referring to FIG. 3, one of the posts 40 is shown in a perspective view. In this embodiment, all of the posts 40 in the assembly (i.e. six posts 40) are identical. The post 40 includes a shaft portion 41 and a head portion 42. The head portion 42 has an inclined surface 43, angled at 60° with respect to the longitudinal axis in this embodiment (i.e. 30° with respect to a plane perpendicular to the longitudinal axis). The shaft portion 41 includes an end portion 44 opposite the head portion 42, having a reduced diameter for engaging the back plate 50. The head portion 42 has a larger cross-sectional dimension than the shaft portion 41 in a plane perpendicular to the longitudinal axis. The head portion 42 has side surfaces 47 that are adjacent to the side surfaces of an adjacent post when assembled to form the drive unit 4. In order to avoid a short-circuit of the magnetic flux between the posts 40, a small air gap or other type of insulation is provided between the head portions 42. Further to avoiding a short-circuit, it may be advantageous to provide an insulation material between the head portions 42 of the posts 40 that keeps the magnetic field within each of the posts 40. In other words, the head portions 42 may be separated by a magnetically insulating material. For instance, magnets, e.g. plates of a magnetic material, can be arranged between the head portions 42 to separate the head portions 42 and the respective magnetic fields from each other. Radially inner surfaces 48 of the post head portions 42 form a central opening 54. It will be appreciated that the transition surface between the surfaces 43 and 48 does not need to be rounded.

Different views of another embodiment of a post 40 are shown in FIG. 4, which corresponds to the previous embodiment except for slight changes in the shape of the shaft portion 41 and the head portion 42. FIG. 4a shows a cross-sectional view along the line A-A illustrated in FIG. 4d, which shows a top view (i.e. towards the head portion 42) of the post 40. FIG. 4b shows a perspective view of the post 40, while FIG. 4c shows a bottom view (i.e. a view towards the end portion 44 of the shaft portion 41). The post 40 may have an overall length of about 9 to 10 mm, wherein the head portion 42 may have a length of about 2 mm. In this embodiment, the head portion 42 has a surface 43 which is inclined at an angle of 45° with respect to the axis of rotation or longitudinal axis. Accordingly, the angle 45 between the surface 43 and a ledge 49 shown in FIG. 4a is 135°. The ledge 49 may serve as a stop when the posts 40 are assembled in a housing. Furthermore, a shoulder 46 is formed by the head portion 42, which may serve as a stop for a coil winding. As described in connection with FIG. 3, the head portion 42 comprises side surfaces 47 and a radial inner surface 48.

Figure 5:
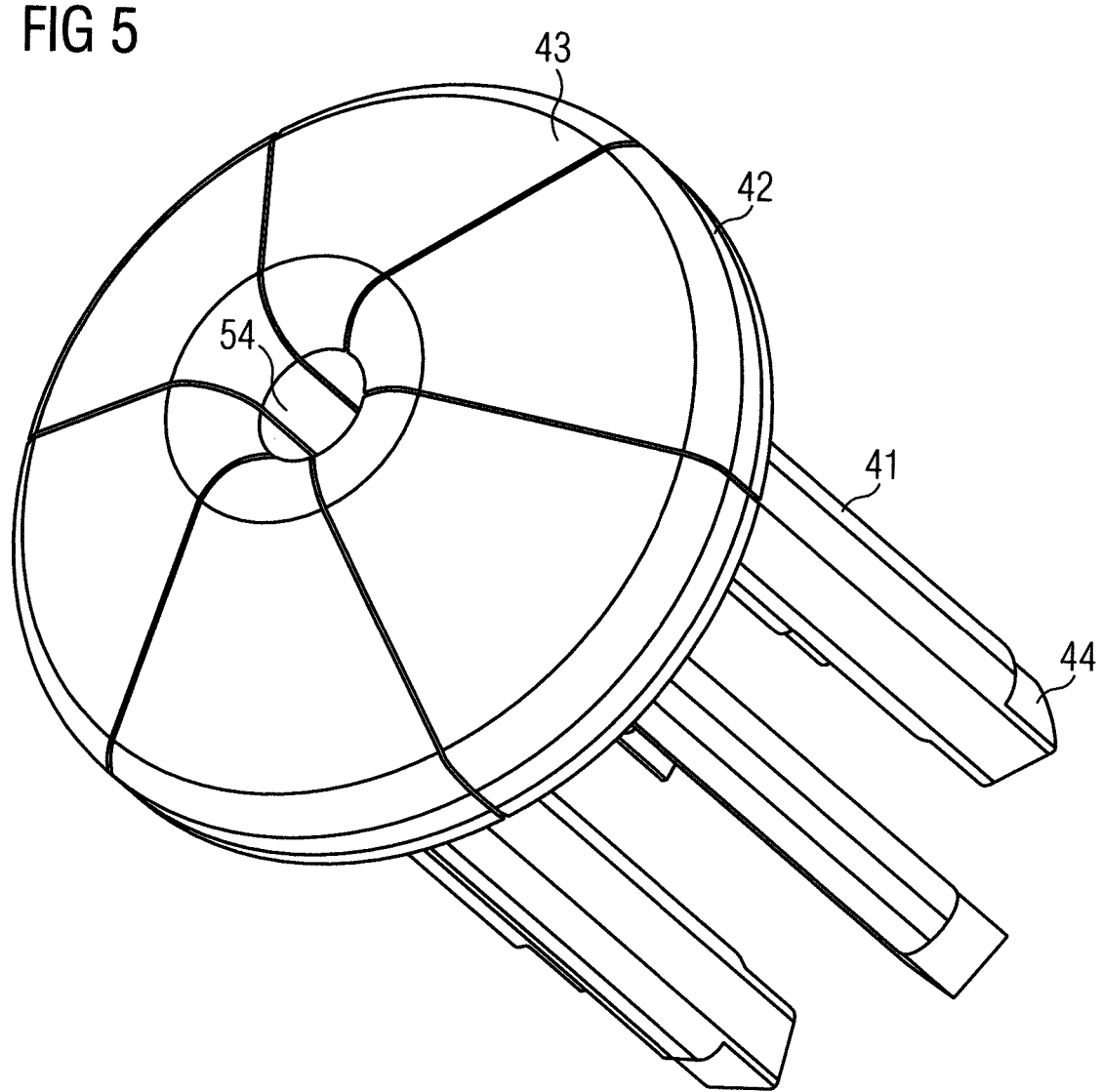
FIG. 5 shows an arrangement including six posts.
Figure 6:
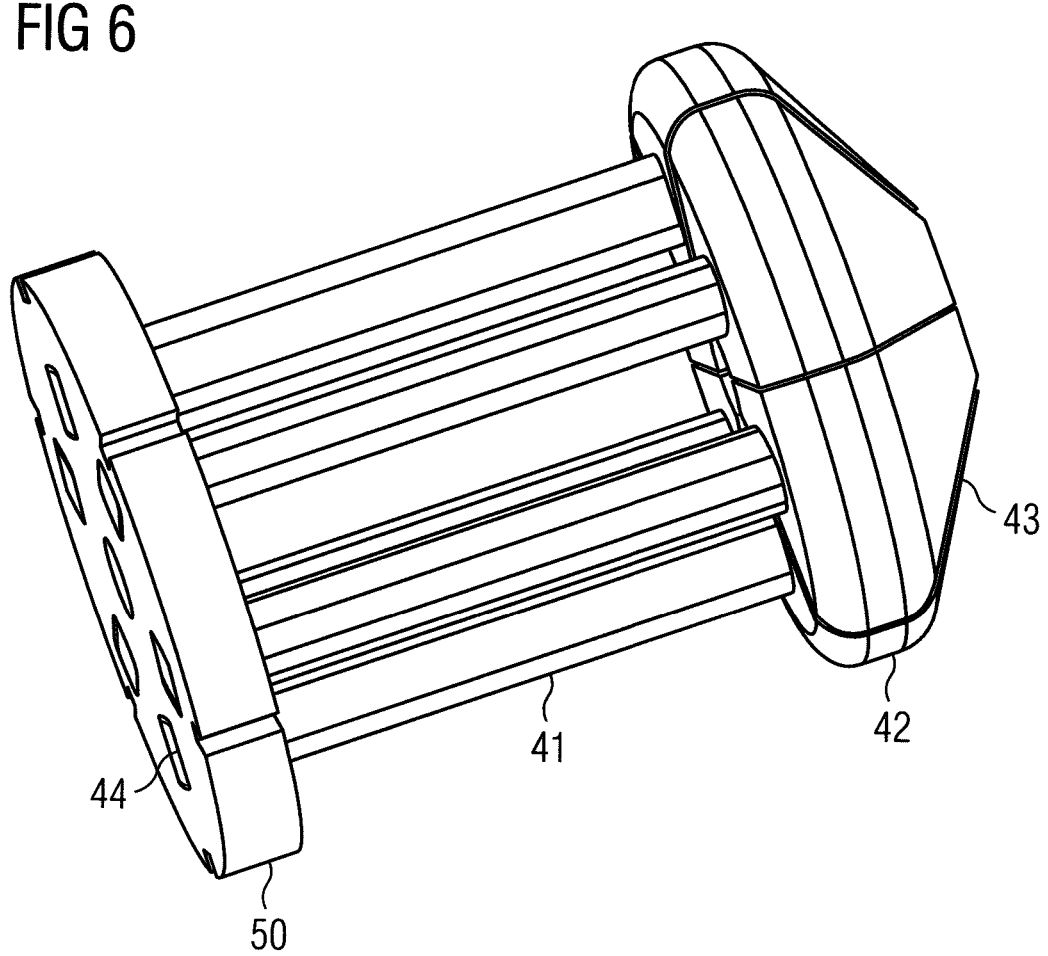
FIG. 6 shows the arrangement of FIG. 5 along with a back plate.

FIG. 5 illustrates an assembly including six posts 40, described in connection with FIG. 3. All posts 40 are formed identically, such that each head portion 42 forms a 60° segment of a circle, that is to say, a "pie slice" of 60°. It will be appreciated that the assembly may include fewer or more posts, such as two, three, four or five or more than six, where the angle depends on the number of posts, e.g. four posts that each form a 90° segment or eight posts that each form a 45° segment. As already mentioned above, the number of posts 40 is preferably even, where diametrically opposed posts 40 may form a pair, e.g. with respect to control of the magnetic field, i.e. each pair of posts may be controlled as a unit to activate the posts of each respective pair simultaneously. The head portions 42 form a cone having a conical surface formed by the inclined surfaces 43. This can be seen more clearly in FIG. 6. In FIG. 6, the reduced-diameter end portions 44 of the shaft portions 41 are mounted in the back plate 50.

Figure 7:
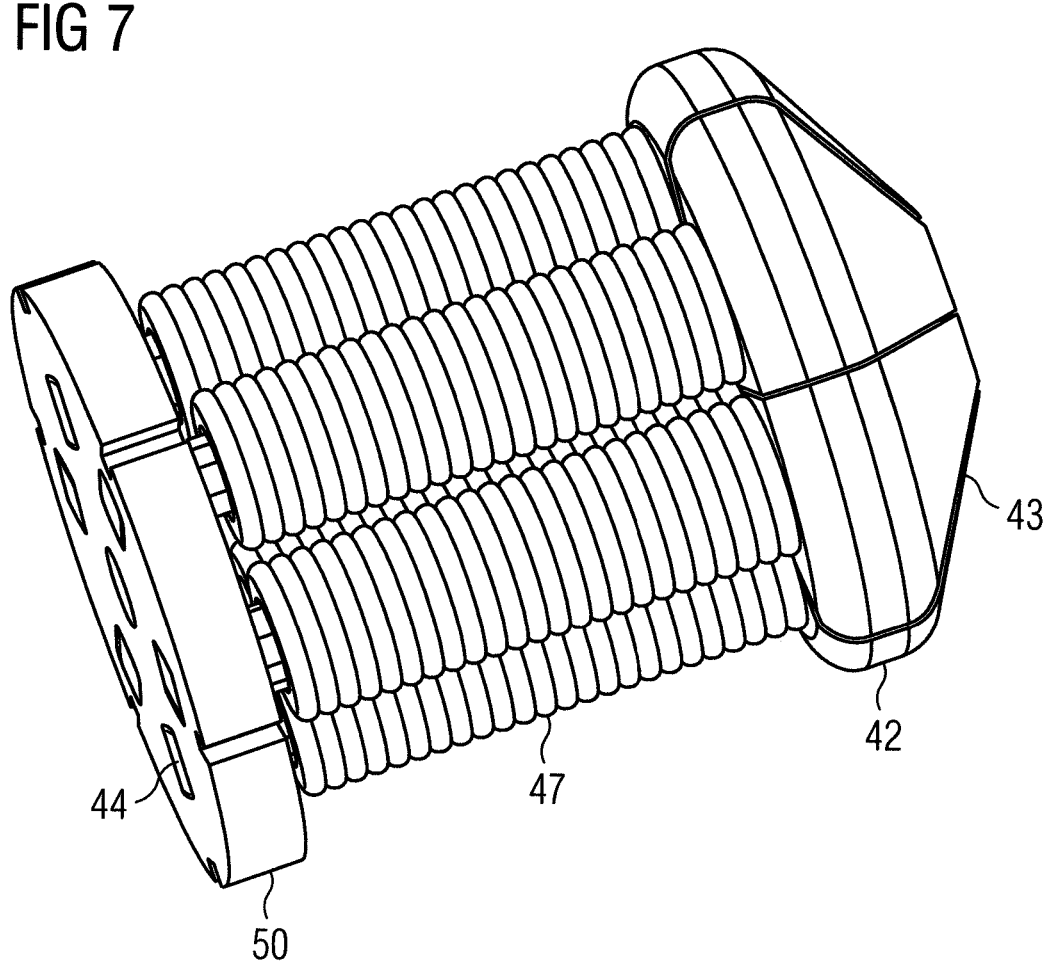
FIG. 7 shows the arrangement of FIG. 6 along with coil windings.
Figure 8:
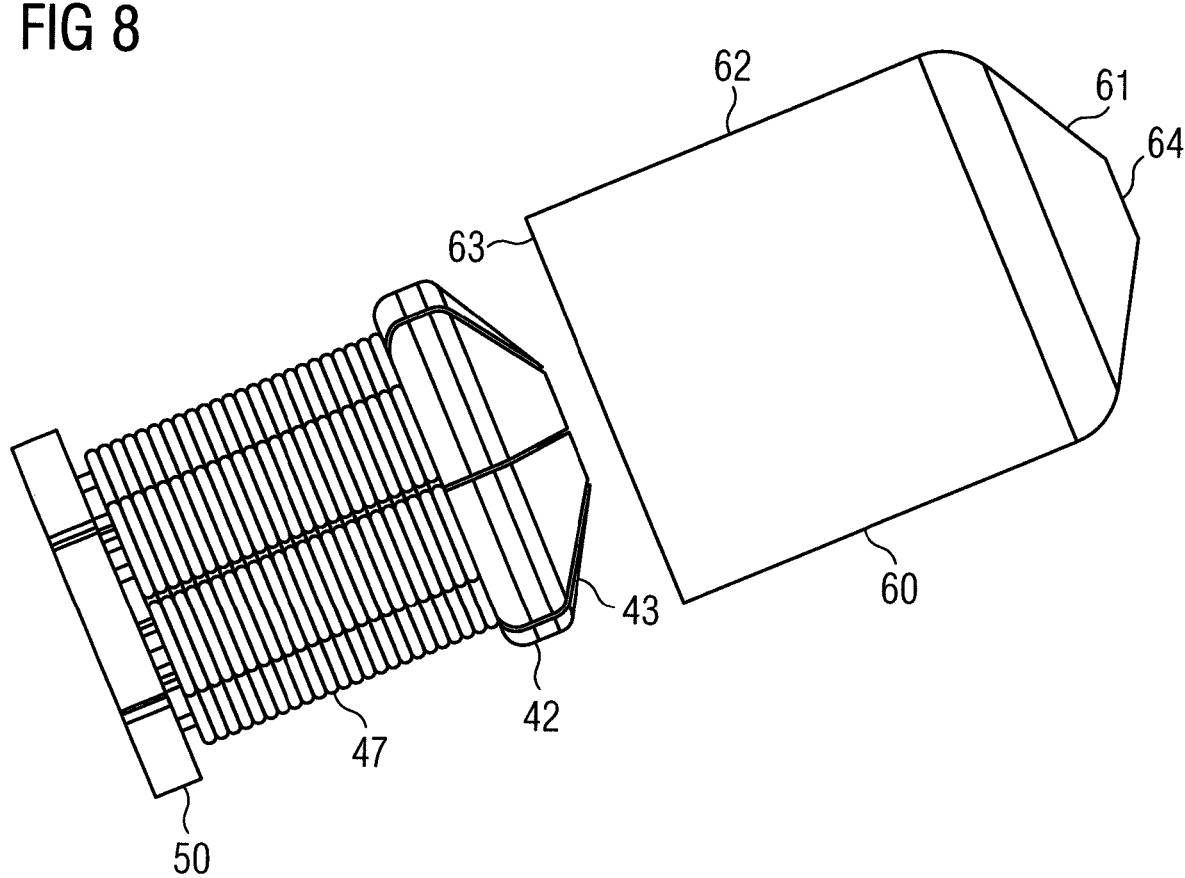
FIG. 8 shows the arrangement of FIG. 7 along with a housing.

In FIG. 7 the same arrangement is illustrated including coil windings 47 about the posts 40. The coil windings 47 do not extend radially beyond the head portions 42, thereby providing for a compact outer dimension. It will be appreciated that preferably the maximum cross-sectional area defined by the head portions 42 is used for the coil windings 47 to optimize usage of the available space and to minimize air gaps that act as an insulator and affect the magnetic flux. Suitable materials for the coil windings are e.g. copper or silver. Further, the diameter of the shaft portions 41 of the posts 40 is chosen so as to optimize the number of windings of the coil windings 47. FIG. 8 shows a housing 60 which is to be mounted over the post arrangement. The housing 60 conforms to the shape of the post arrangement and comprises a substantially cylindrical portion 62 and a conical end portion 61. The conical end portion 61 is tapered at the same angle as the conical surface formed by the inclined surfaces 43 of the posts' head portions 42, that is to say, the angle preferably is between about 30° to 60°, preferably 30° or 45°, with respect to a plane perpendicular to the longitudinal axis. The housing 60 is closed by the back plate 50 at an open end 63 opposite the conical end portion 61. The conical end portion 61 has a central opening 64 that is aligned with the central opening 54 formed by the posts 40 and a central opening 53 in the back plate 50.

The back plate 50 is illustrated in more detail in different views in FIG. 9 (top view in FIG. 9a, cross-sectional view along line A-A in FIG. 9b, and cross-sectional view along line B-B in FIG. 9c). The back plate 50 has apertures 51 for receiving the reduced-diameter end portions 44 of the shaft portions 41 of the posts 40. Preferably, the number of apertures 51 in the back plate 50 corresponds to the number of posts 40 of the drive unit 4. In the embodiment shown, six apertures 51 are disposed at a regular distance of 60° about the axis of rotation 10, with each of the apertures 51 being at the same distance from the axis of rotation 10. The apertures 51 are shown as extending completely through the back plate 50 in the cross-sectional view of FIG. 9c. However, the apertures 51 may alternatively extend into the back plate 50 only up to a certain depth rather than completely through the back plate 50. A central opening 53 is formed for receiving the bearing pin 15, as described above. The back plate 50 is made of a magnetic material, preferably cobalt steel, to close the magnetic flux path. The diameter of the back plate 50 may be about 5 to 7 mm. Furthermore, notches 52 are provided at the periphery of the back plate 50 for receiving wires 56 to connect the coil windings 47 to a control unit 55, such as a printed circuit board (PCB) at the back of the back plate 50, as shown schematically by dashed lines in FIG. 9b.

Referring to FIG. 10, the magnet 32 of the impeller 3 (see FIG. 2) is shown in a top view (FIG. 10a), a cross-sectional view (FIG. 10b) and a perspective view (FIG. 10c). In this embodiment, six magnets 32 are provided that are arranged uniformly about the axis of rotation 10, with the orientation of the respective magnetic field alternating. Fewer or more magnets, such as four, eight, ten or twelve magnets, may be provided. The magnets 32 form a recess 35 having a surface 33. The recess 35 corresponds in size and shape to the conical surface formed by the surfaces 43 of the head portions 42 of the posts 40, as shown best in FIG. 6, taking into account the housing 60 that surrounds the drive unit 4, in particular the conical end portion 61 (FIG. 8). It will be appreciated that this includes that the distance between the impeller 3 and the drive unit 4 may not be constant but may increase towards the axis of rotation 10 as explained above. The recess 35 in this embodiment has a conical shape with an angle 34 of 45° with respect to the axis of rotation 10 or longitudinal axis. Other angles, such as 60°, are possible, depending on the shape of the drive unit 4, in particular the end surface formed by the head portions 42 of the posts 40. Furthermore, the magnets 32 form a central opening 36 for receiving the bearing pin 15, as shown in FIG. 2. The central opening 36 is aligned to the central opening 54 of the drive unit 4. As shown in FIG. 10b, the magnetic flux of the magnets 32 is closed by the yoke 37. The yoke 37 may have any suitable shape depending on the shape of the impeller 3, such as conical as shown in FIG. 2 or disc-shaped as indicated in FIG. 10b. Optionally, an encapsulation 38 is provided that encloses the magnets 32 and, if applicable, the yoke 37 to protect the magnets 32 and yoke 37 against corrosion.

Figure 11:
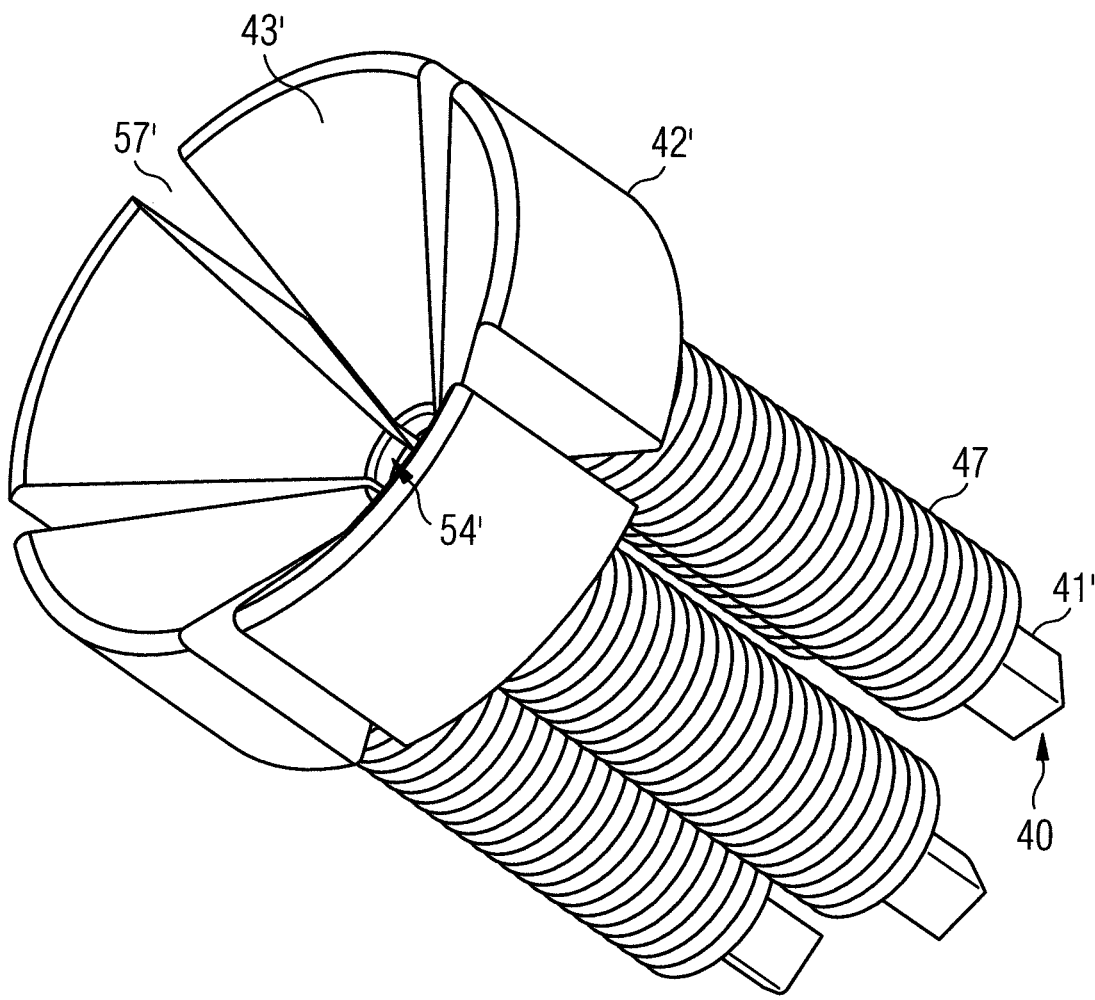
FIG. 11 shows another embodiment of a drive unit.

In FIG. 11 is illustrated another embodiment of a drive unit which is substantially similar to the aforementioned embodiments. The arrangement includes six posts 40' having a respective coil winding 47 on their shaft portions 41'. As in the previous embodiments, there may be fewer or more posts 40'. The posts 40' are preferably attached to a back plate (not shown) as in the previous embodiments. The posts 40 each include a head portion 42', which has a different shape from the above described head portions 42. Although the angle may be the same as described above, the inclined surfaces 43' face radially inwards rather than radially outwards. That is to say, the head portions 42' form a substantially conical recess. It will be appreciated that the magnet of the impeller will be shaped accordingly, i.e. the magnet will have a corresponding conical shape rather than a conical recess as in the previous embodiments. As in the previous embodiments, the drive unit has a central opening 54'. The posts 40' in the embodiment of FIG. 11 are separated by gaps 57' that prevent a bypass or short-circuit between the posts 40', whereas the head portions 42 of the posts 40 in the previous embodiments are shown to be directly adjacent to each other or separated only by small gaps. It will be appreciated, however, that a short-circuit between the posts is to be avoided in all embodiments.

Figure 12:
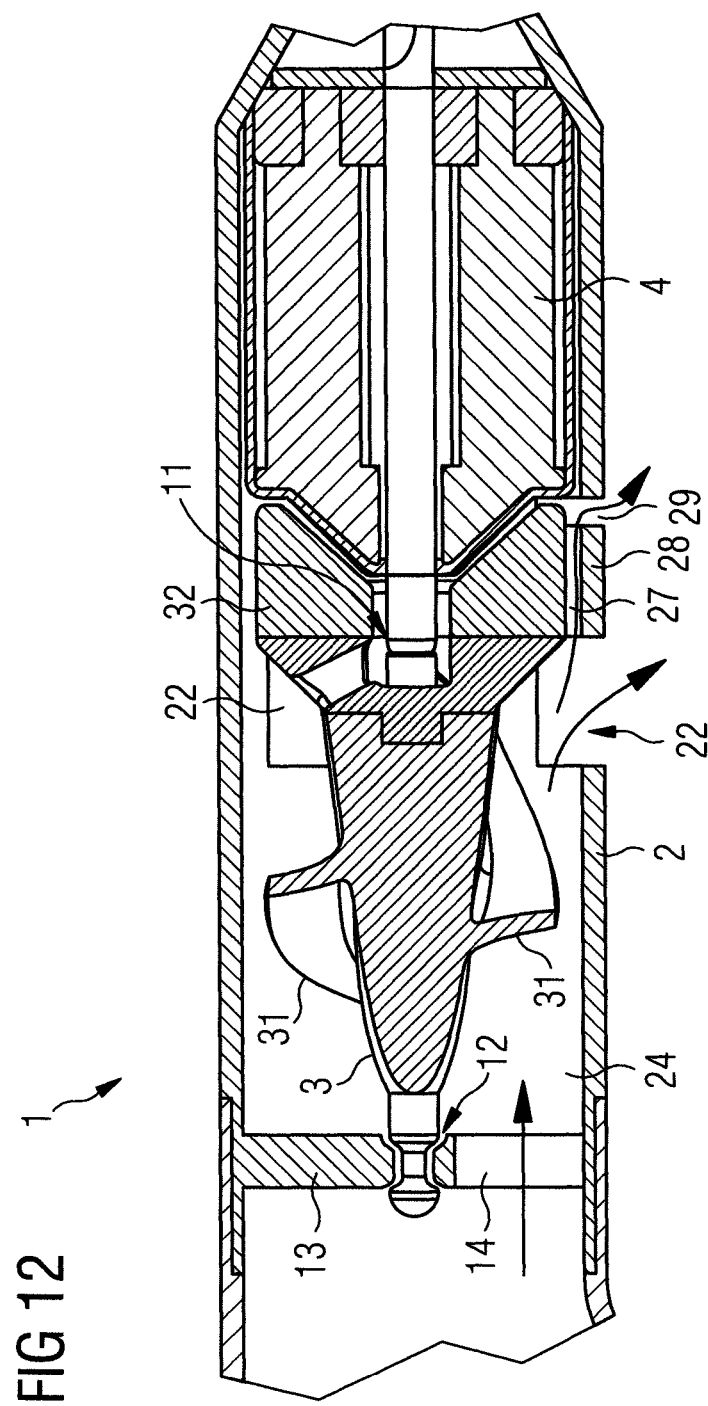
FIG. 12 shows another embodiment of a blood pump.

With reference to FIG. 12, another embodiment of a blood pump 1 is shown, which is similar to that of FIGS. 1 and 2. In contrast to the above embodiment, the blood pump 1 of FIG. 12 has an additional radial hydrodynamic bearing. A circumferential portion 28 of the pump casing 2 or sleeve is provided to form a gap 27 between the impeller 3 and the circumferential portion 28. In addition to the blood flow outlet 22 a further blood flow outlet 29 allows blood to flow through the gap 27 and out of the pump casing 2. The size of the gap 27 is chosen so as to form a radial hydrodynamic bearing.

Figure 13A:
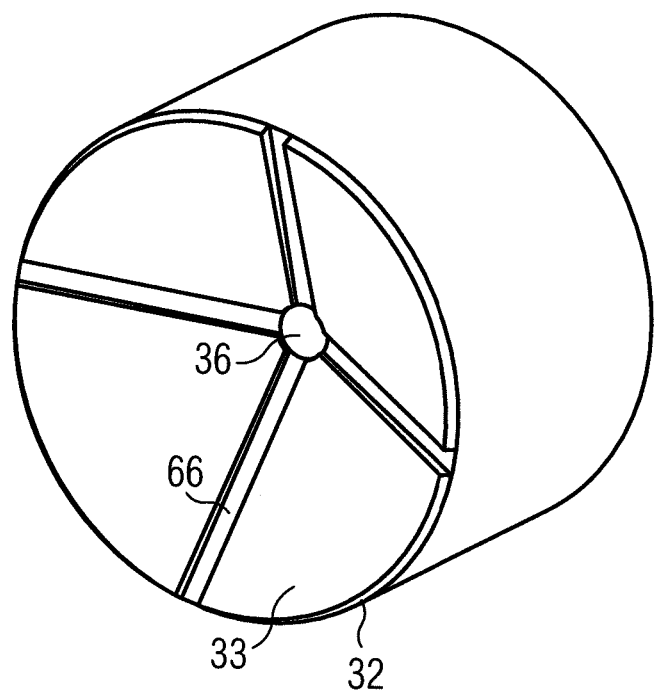
FIGS. 13a and 13b show different views of a drive unit and impeller magnets according to another embodiment.
Figure 13B:
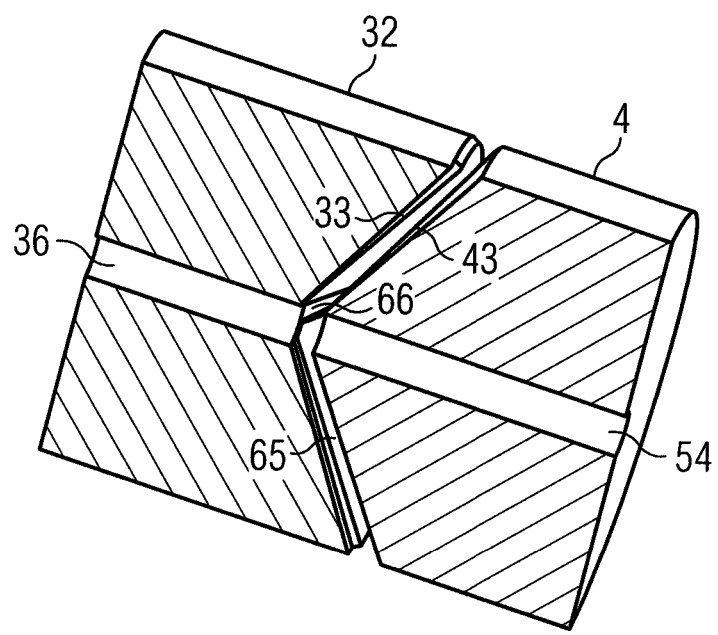

FIGS. 13a and 13b schematically illustrate the magnets 32 of the impeller and the magnets 32 arranged with respect to the drive unit 4. In this embodiment, four magnets 32 are provided that are separated by respective gaps 66. The gaps 66, which may be formed as channels between the surfaces 33 of the magnets 32, extend in a radial direction from the central opening 36 towards the outer perimeter of the magnets 32. As will be described in more detail below with reference to FIGS. 15a and 15b, the reduction of the size of the magnets 32 does not cause a loss of efficiency of the magnetic coupling. FIG. 13b illustrates the relative arrangement of the magnets 32 and the drive unit 4, where a gap 65 is provided between the drive unit 4 (i.e. the stator) and the magnets 32 of the impeller (i.e. the rotor). The channels or gaps 66 improve washing of the gap 65 since they cause a centrifugal pump effect for the blood.

Figure 14A:
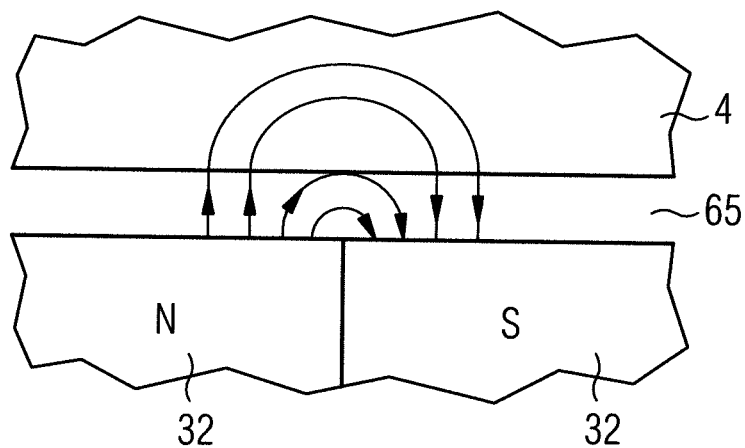
FIGS. 14a and 14b schematically illustrate magnetic field lines between magnets of the impeller.
Figure 14B:
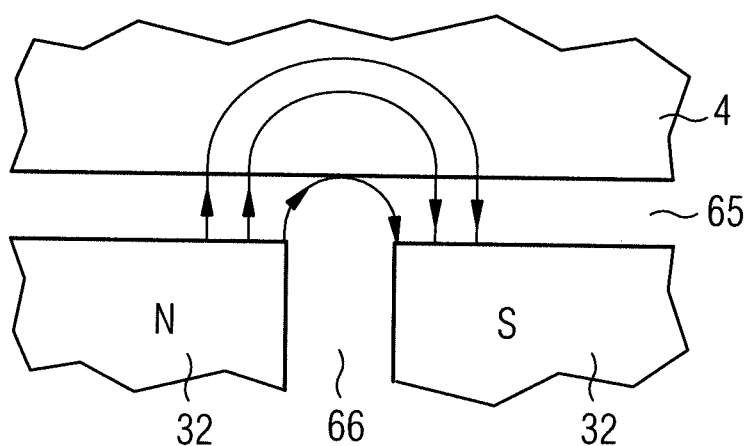

With reference to FIGS. 14a and 14b, the principle of the magnetic coupling between the rotor, in particular the magnets 32, and the stator, i.e. the drive unit 4, is schematically illustrated. In FIG. 14a, the magnets 32 are not or substantially not separated by a gap. Some exemplary magnetic field lines from north N to south S are illustrated. Due to the gap 65 between the drive unit 4 and the magnets 32 the innermost magnetic field lines do not interact with the drive unit 4. That is to say, this part of the magnetic field does not contribute to the drive of the impeller. Thus, no efficiency of the magnetic coupling will be lost if a gap 66 is provided between the magnets 32. In FIG. 14b, the same amount of magnetic field lines reaches the drive unit 4 as in FIG. 14a. As a skilled person knowing the orientation of magnetic field lines is able to calculate, the size of the gap 66 is directly dependent on the size of the gap 65.

With reference to FIG. 15, another embodiment of a drive arrangement for a blood pump is shown. The drive unit 4, including the posts 40 with coil windings 47, is substantially the same as described above. Like reference numerals refer to like parts. As in the previous embodiments, the drive unit 4 includes a back plate 50. However, the design of the impeller is different. In FIG. 15 only the magnets 32 and the yoke 37 of the impeller are shown. The impeller has an increased diameter, in particular a larger diameter than the drive unit 4, and an axial extension 39 such that the extension 39 extends circumferentially about the drive unit 4, in particular in the area of the head portions 42 of the posts 40. This arrangement allows for improved magnetic coupling, as will be explained in the following.

As indicated by some exemplary schematic magnetic field lines, the extension 39 causes the magnetic coupling between the magnets 32 and the drive unit 4 to occur not only in the region of the inclined surfaces 43 but also in the region of the outer side surfaces of the head portions 42 of the posts 40. In this region, the magnetic field lines extend in a substantially radial direction between the blood pump's rotor and stator and a high torque can be created to drive the impeller. As also illustrated in FIG. 15, as in all other embodiments, the magnetic field lines form a closed loop that extends through the posts 40, including the head portions 42 and the shaft portions 41, through the magnets 32 and through both end plates or yokes 50 and 37.

Figure 16:
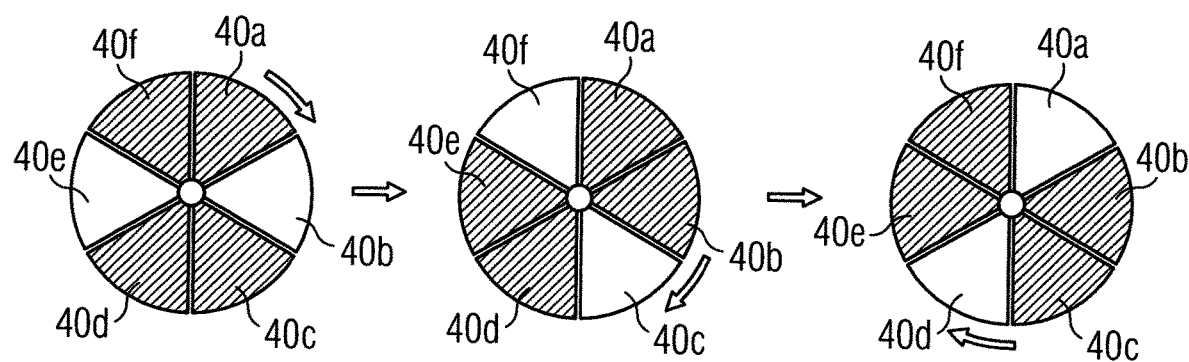
FIG. 16 schematically illustrates an operating mode of the drive unit.

With reference to FIG. 16, the operating mode of the drive unit is schematically illustrated in an example having six posts 40a, 40b, 40c, 40d, 40e and 40f. In order to create a rotating magnetic field, the posts are controlled sequentially. The posts are controlled in pairs to establish a balanced rotation of the impeller, in which diametrically opposing posts 40a and 40d, 40b and 40e, and 40c and 40f respectively form pairs. The magnetic density can be increased by activating four of the six posts at the same time. FIG. 13 illustrates a sequence with three steps, in which the activated posts are marked. In the first step, the posts 40a, 40c, 40d and 40f are activated, i.e. a current is supplied to the respective coil winding to create a magnetic field. In the second step, the posts 40a, 40b, 40d and 40e are activated, while in the third step, the posts 40b, 40c, 40e and 40f are activated. This sequence is repeated to create the rotating magnetic field.

FIGS. 17 to 21 illustrate embodiments which are substantially similar to the aforementioned embodiments with the main difference that the parts of the drive unit are not formed as a solid body but are slotted or otherwise formed by a discontinuous material as will be described in more detail below. It will be appreciated that the features and functions described above with respect to FIGS. 1 to 16 are likewise applicable for the following embodiment. Thus, like reference numerals enhanced by 100 refer to like parts of the blood pump, drive unit and other parts of the blood pump. Vice versa it will be appreciated that the aforementioned embodiments may be provided with slotted components or discontinuous soft magnetic material as will be described below.

Figure 17:
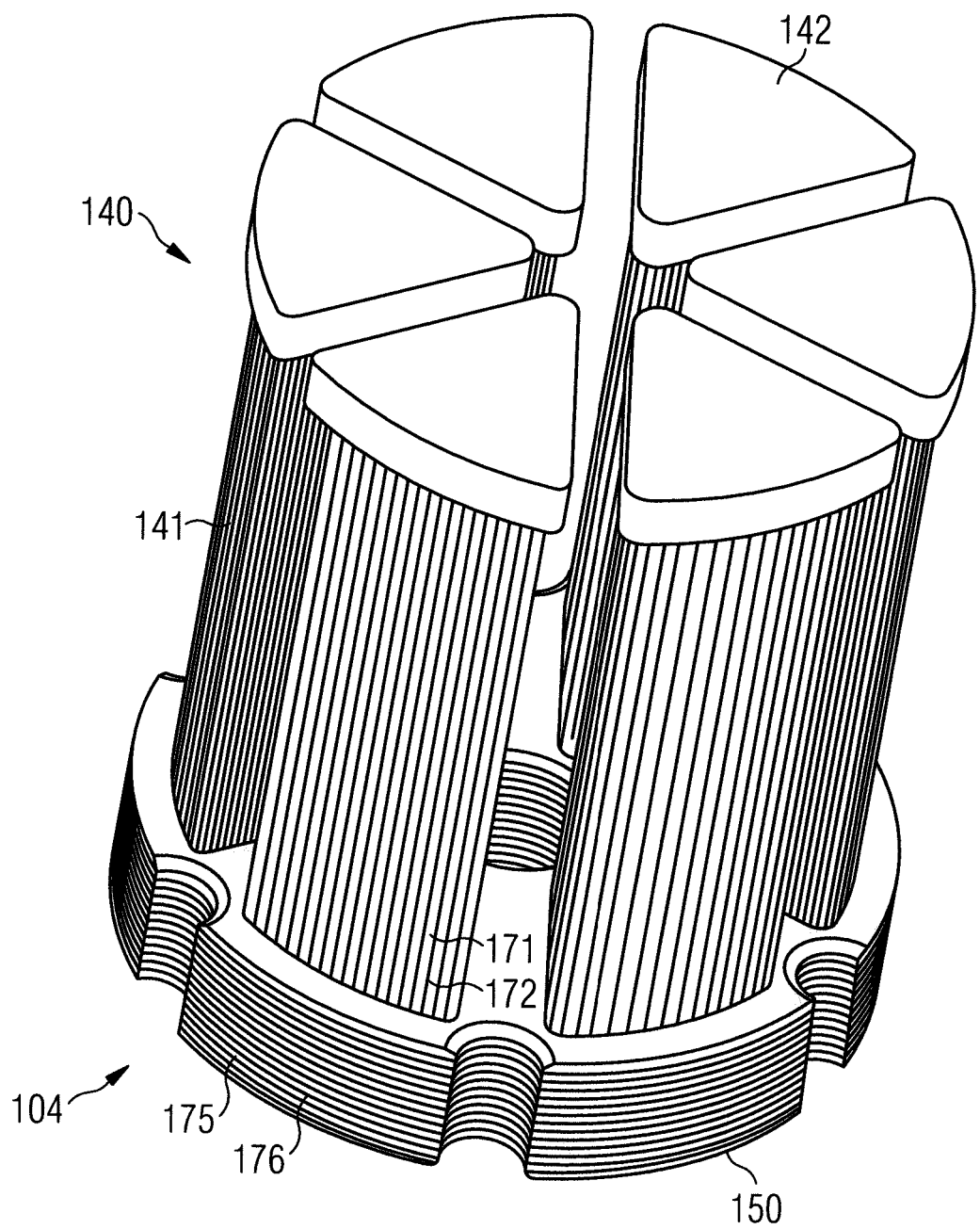
FIG. 17 shows another embodiment of a drive unit.

FIG. 17 shows a perspective view of a drive unit 104 without coil windings and magnets similar to the view shown in FIG. 6. The drive unit 104 comprises six posts 140 each having a shaft portion 141 and a head portion 142 as explained above with respect to the previous embodiment. The posts 140 are attached to a back plate 150 similar to the previous embodiment. The head portions 142 have a flat top surface that extends in a plane perpendicular to the axis of rotation, i.e. the longitudinal axis of the drive unit 104.

In contrast to the above described embodiments, components of the drive unit 104, more specifically the shaft portions 141 of the posts 140 as well as the back plate 150 comprise a soft magnetic material that is discontinuous in respective cross-sections transverse to the direction of the magnetic flux (see FIG. 15 for a schematic illustration of the magnetic flux). In particular, the shaft portions 141 and the back plate 150 are slotted, i.e. they are formed of a stack of sheets of soft magnetic material that are electrically insulated from each other. The sheets may have a thickness from about 50 µm to about 350 µm, e.g. 100 µm. The insulating layers may have a thickness of about 1 µm to about 50 µm. Optionally, the head portions 142 may be slotted, too, as will be described in more detail below.

The shaft portions 141 are formed of sheets 171 insulated from each other by insulating layers 172, and the back plate is formed of sheets 175 insulated from each other by insulating layers 176. The sheets 171 of the shaft portions extend parallel to the axis of rotation, as can be seen also in FIGS. 19a to 19d, so as to provide a discontinuous cross-section transverse to the axis of rotation. The back plate 150 is formed of sheets 175 that extend in planes perpendicular to the axis of rotation so as to provide a discontinuous cross-section parallel to the axis of rotation. It will be appreciated that the back plate 150 may be formed of a solid material, i.e. may not be slotted. The slotted construction reduces eddy currents and, thus, heat generation and energy loss, i.e. energy consumption.

Figure 18:
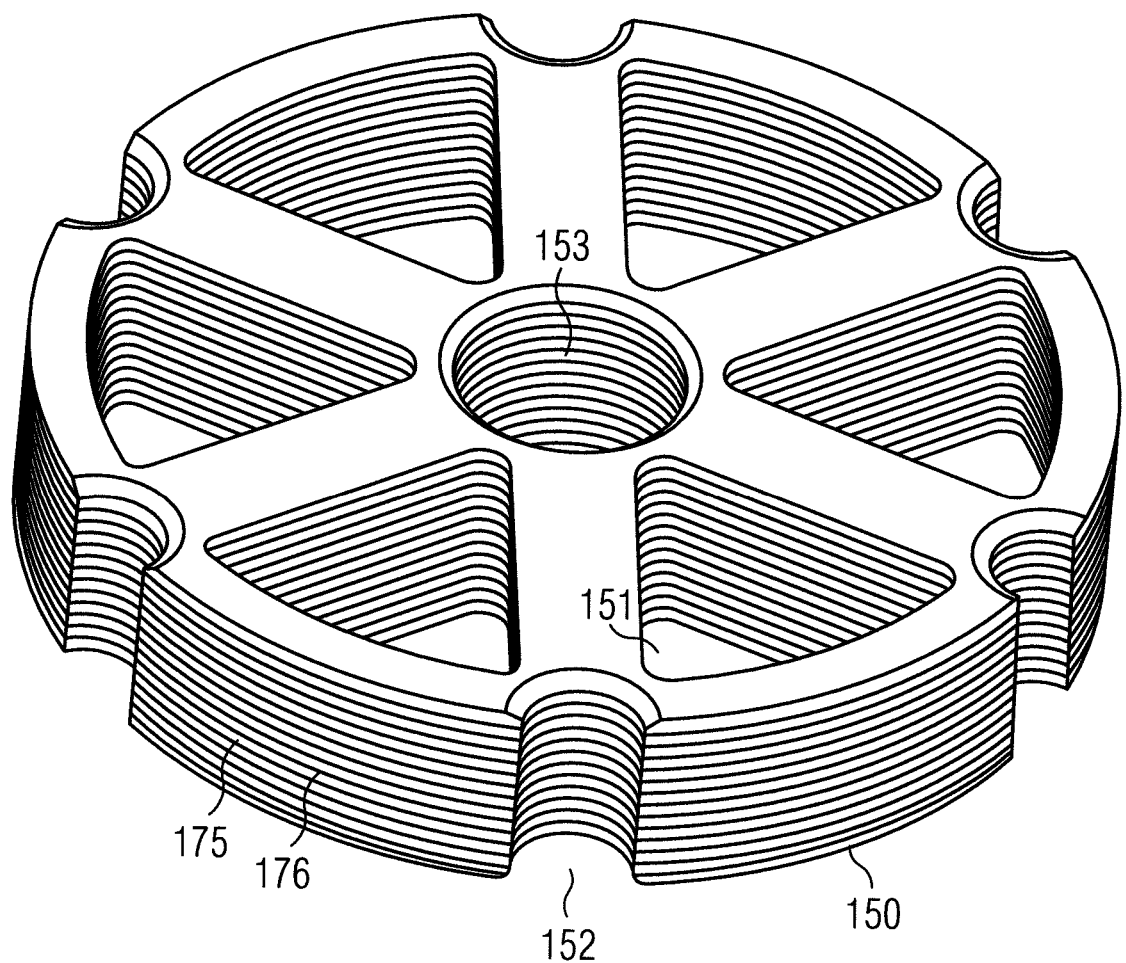
FIG. 18 shows the back plate of the drive unit of FIG. 17.
Figure 19A:
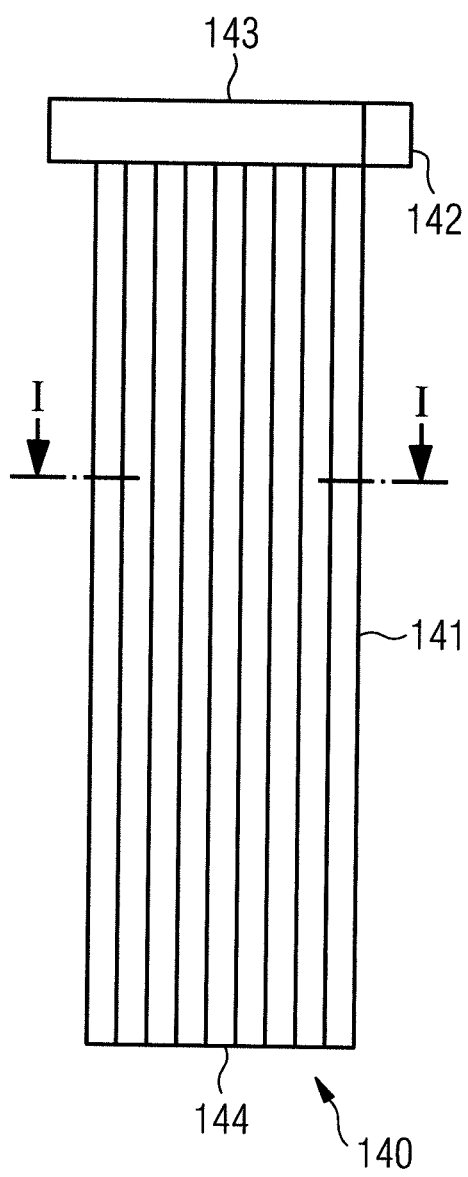
FIG. 19a shows a side view of a post of the drive unit of FIG. 17.
Figure 19B:
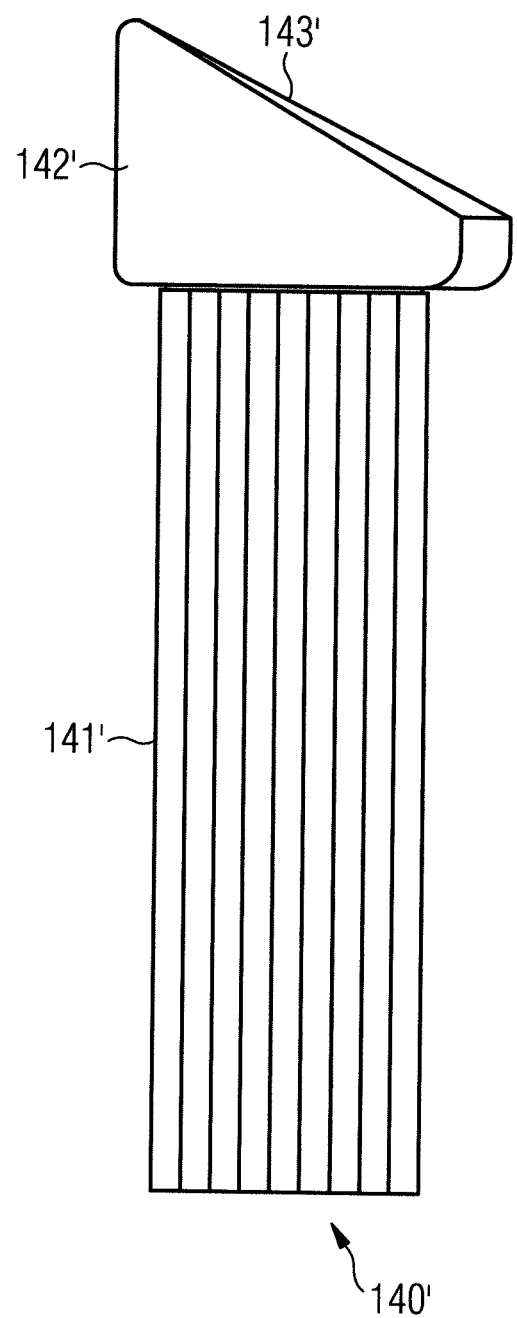
FIG. 19b shows another embodiment of a post.

FIG. 18 shows the back plate 150 in more detail. Similar to the back plate shown in FIG. 9, the back plate 150 has a central opening 153 and notches 152. As explained above, the back plate 150 is made of a plurality of stacked sheets 175 insulated from each other by insulating layers 176. FIG. 19a shows one of the posts 140 in more detail, having the shaft portion 141 and the head portion 142 with a top surface 143. The top surface is not inclined. Ends 144 of the posts 140 fit into the openings 151 in the back plate 150. In contrast to the embodiment described above, the ends 144 do not have shoulder. The head portion 142 extends laterally beyond the shaft portion 141 such that coil windings do not extend beyond the head portion 142 as explained above. FIG. 19b shows an embodiment of a post 140' with a shaft portion 141' and a head portion 142' in which the top surface 143' is inclined as explained in detail for the previous embodiment.

Figure 19C:
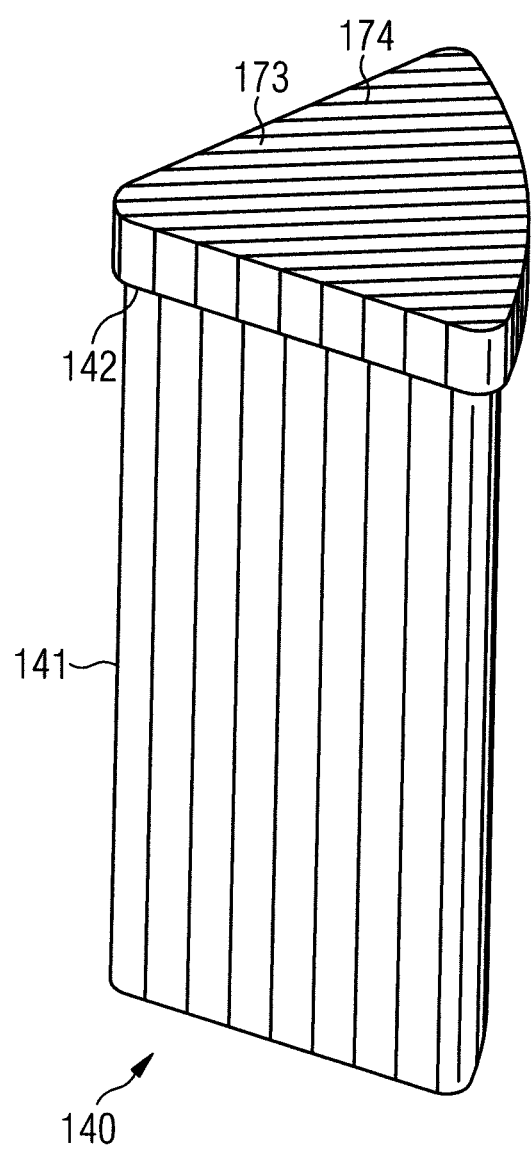
FIG. 19c shows a perspective view of still another embodiment of a post.
Figure 19D:
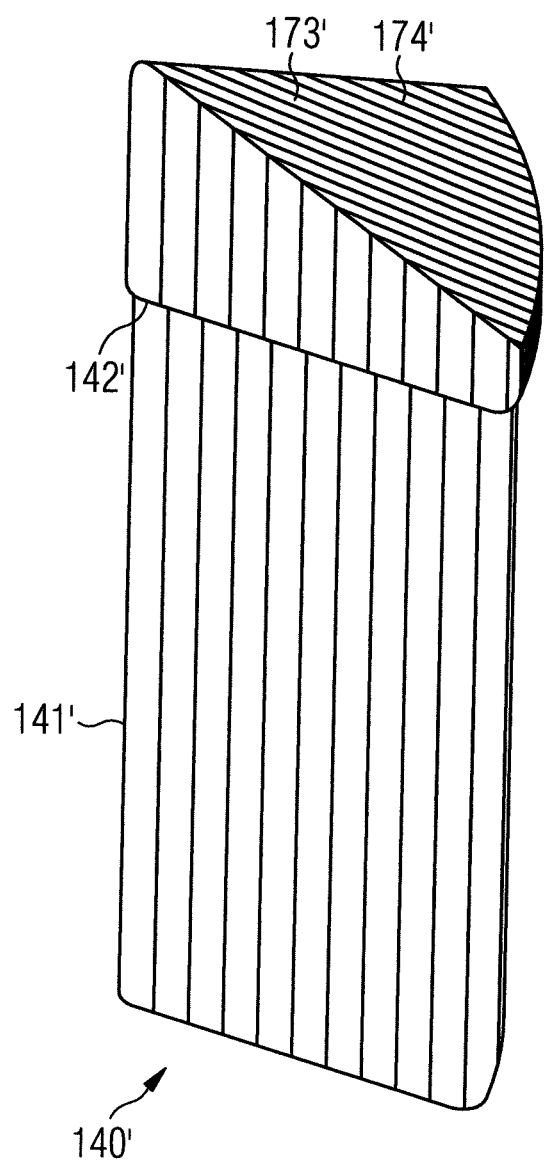
FIG. 19d shows a perspective view of yet another embodiment of a post.

In one embodiment, as shown in FIG. 19c, the head portions 142 of the posts 140 may be formed of a discontinuous soft magnetic material, too. More specifically, the head portion 142 of each of the posts 140 may comprises a soft magnetic material which is discontinuous in cross-section perpendicular to the longitudinal axis of the respective post 40, similar to the shaft portions 141 of the posts 140. The head portions 142 may be formed of sheets 173 insulated from each other by insulating layers 174. Due to the small height of the flat head portions 142, the sheets 173 may also be referred to as "rods". As shown in FIG. 19d, the inclined head 142' may also be formed of a discontinuous soft magnet material, in particular formed of sheets 173' insulated from each other by insulating layers 174'. All characteristics of the discontinuous soft magnetic material described above for the shaft portions 141, 141' may apply for the respective head portions 142, 142'.

Figure 20A:
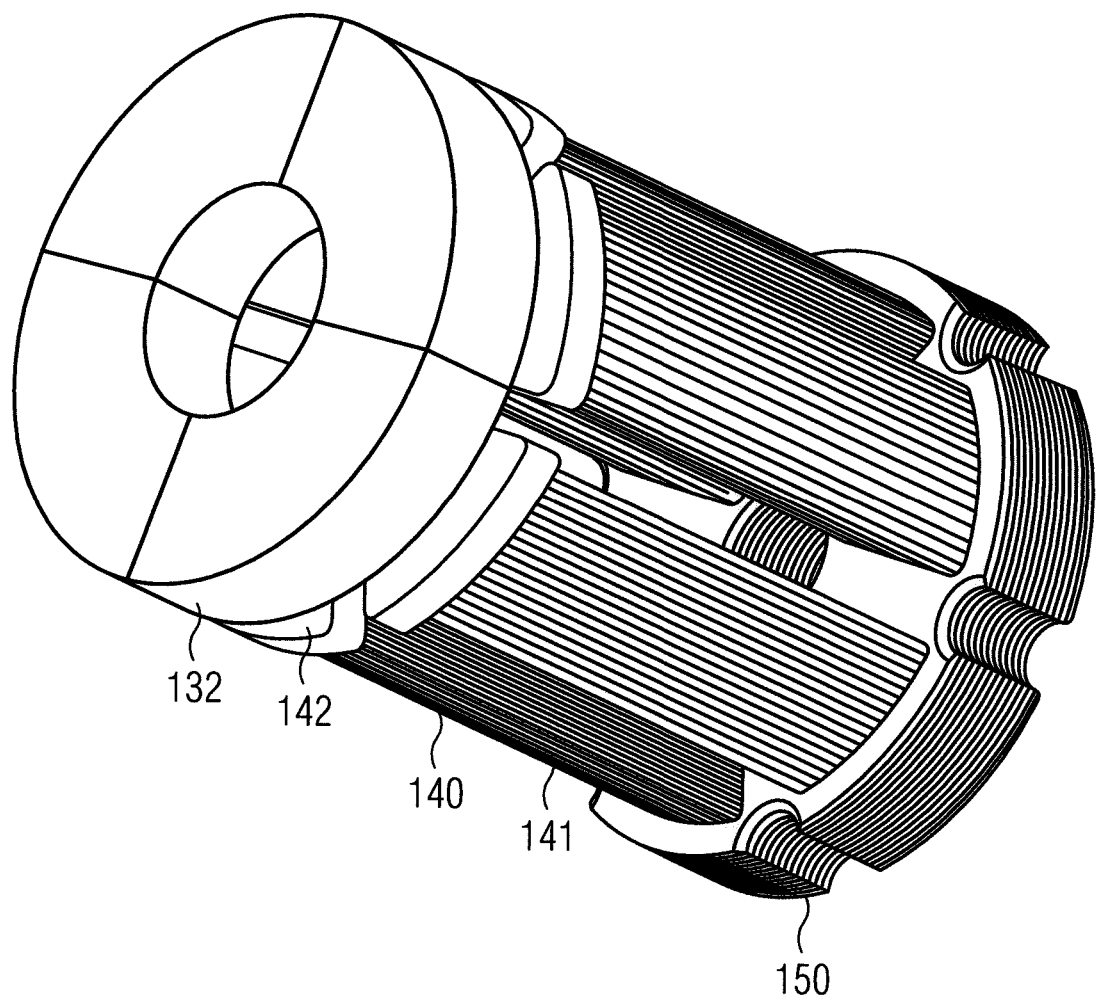
FIGS. 20a and 20b show the drive unit of FIG. 17 with different magnets.
Figure 20B:
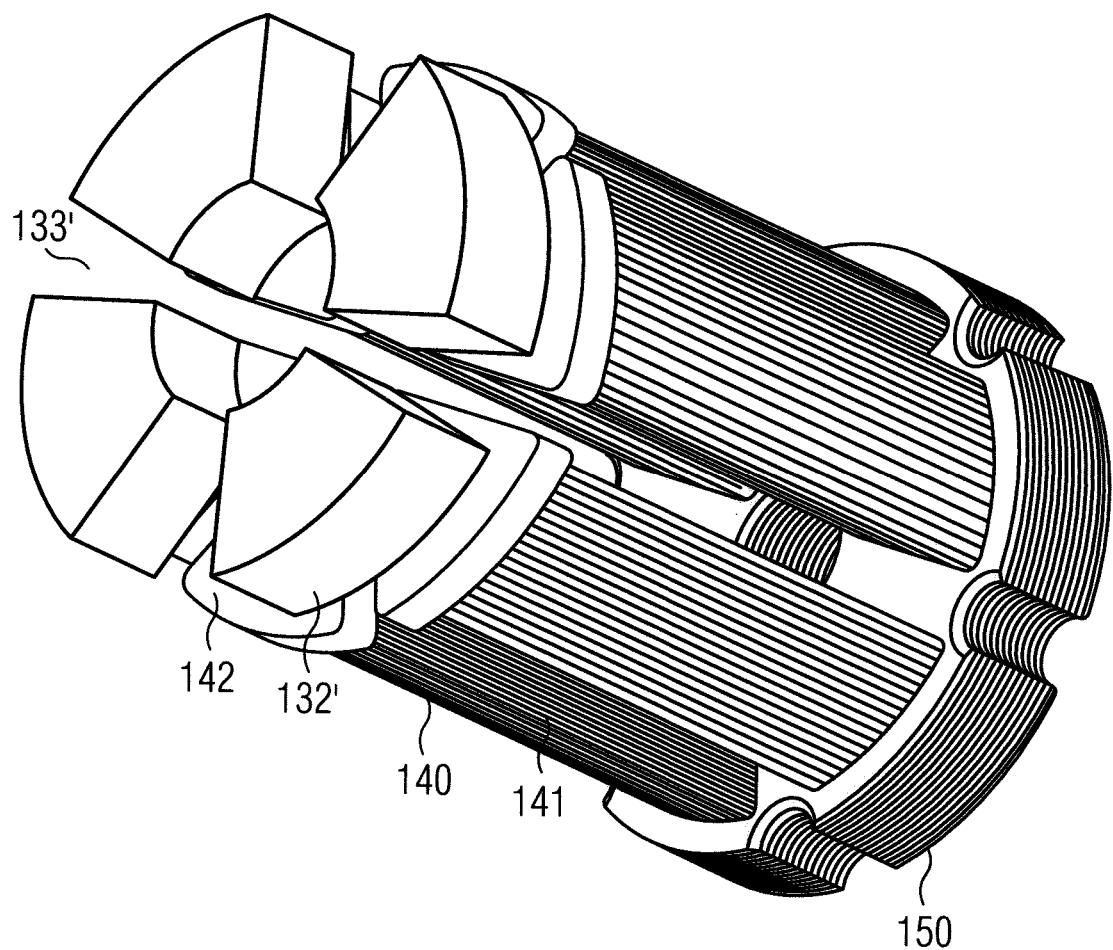

In FIG. 20a, the magnets 132 are illustrated adjacent the head portions 142. Since the top surfaces of the head portions 142 are not inclined, the magnets 132 form a substantially cylindrical component. FIG. 20b shows an alternative embodiment in which the magnets 132' are separated by gaps 133'. As explained above, it has been found that the efficiency of the magnetic coupling does not decrease if the magnets 132' are separated by gaps 133', in particular radially extending gaps, because of the characteristics of the magnetic field and the gap between the drive unit 104 and the impeller.

Figure 21A:
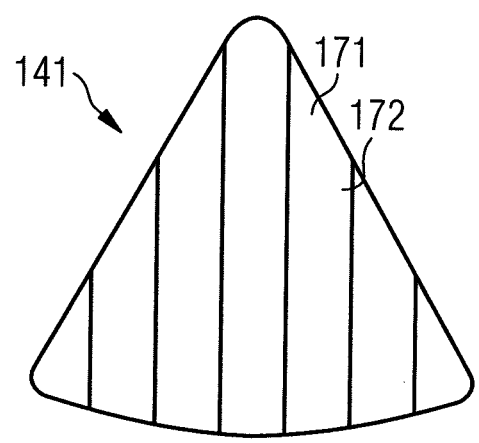
FIGS. 21a to 21j show cross-sections through the shaft portions of posts according to various embodiments.
Figure 21B:
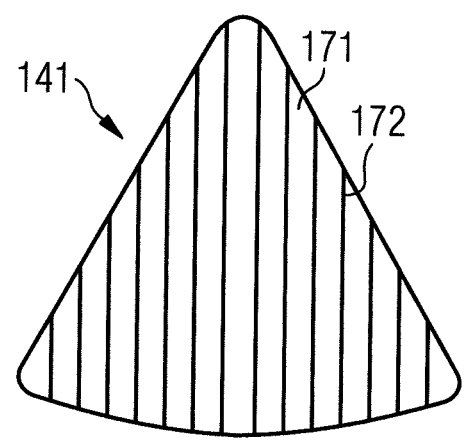
Figure 21C:
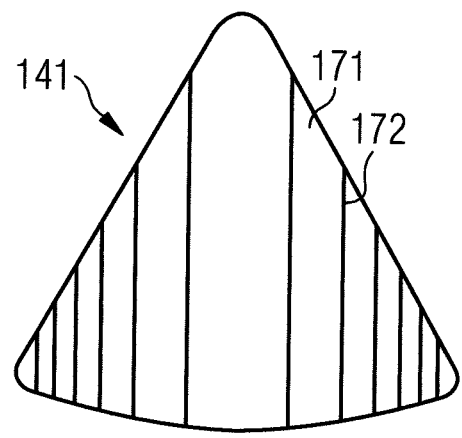
Figure 21D:
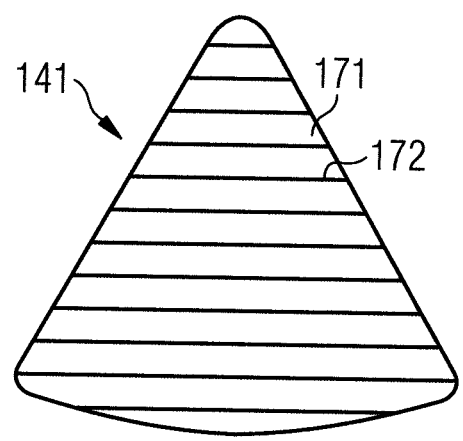

FIGS. 21a to 21j illustrate various embodiments of posts seen in cross-section along the line I-I in FIG. 19a. FIGS. 21a to 21d show embodiments in which the shaft portion 141 of the posts is slotted, i.e. is formed of a plurality of sheets 171 insulated from each other by insulating layers 172. The insulating layers 172 can comprise adhesive, lacquer, baking enamel or the like. FIGS. 21a and 21b show embodiments in which the thickness of the sheets 171 is uniform. The thickness may be in the range from about 25 µm to about 250 µm. The sheets 171 shown in FIG. 21a have a greater thickness than the sheets 171 shown in FIG. 21b. The sheets in FIG. 21c have varying thicknesses, with the central sheet having the greatest thickness and the outermost sheets having the smallest thickness. This may be advantageous because eddy currents in the side regions of the shaft portions are more critical and can be reduced by the thin sheets. Eddy currents in the central area are less critical, and the relatively thick central sheet may help in improving the magnetic flux. The orientation of the sheets 171 may be different as exemplarily shown in FIG. 21d as long as the soft magnetic material in the shown cross-section, i.e. the soft magnetic material in cross-section transverse to the direction of the magnetic flux, is discontinuous or interrupted.

Figure 21E:
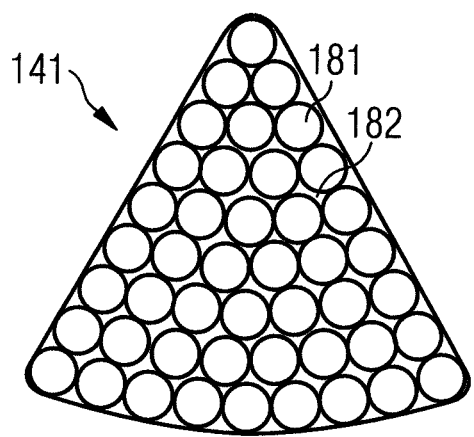
Figure 21F:
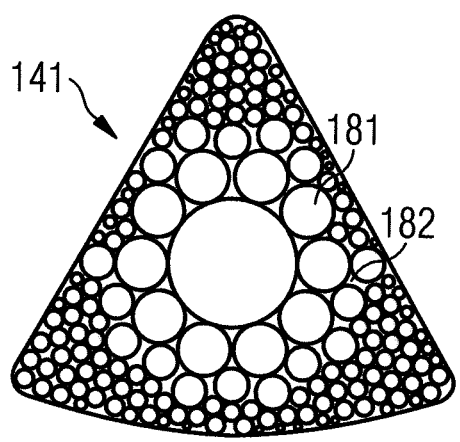
Figure 21G:
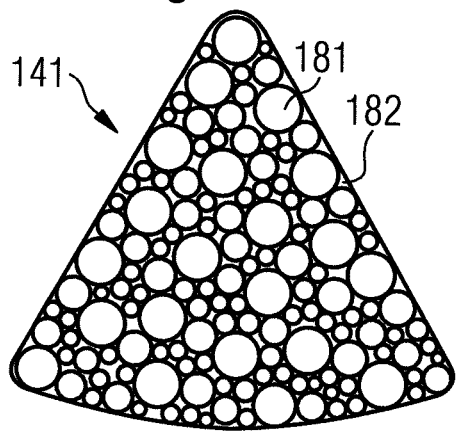
Figure 21H:
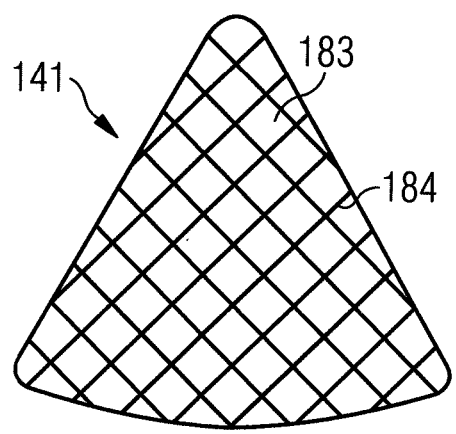

FIGS. 21e and 21f show embodiments in which the shaft portions 141 are formed by a bundle of wires 181 which are insulated from each other by an insulating material 182. The insulating material 182 may be present as a coating of each of the wires 181 or may be a matrix in which the wires 181 are embedded. In the embodiment of FIG. 21e all wires have the same diameter, whereas in the embodiment of FIG. 21f a central wire has a largest diameter and outer wires have smaller diameters, similar to the embodiment shown in FIG. 21c having sheets with varying thicknesses. As shown in FIG. 21g, wires 181 of different diameters may be mixed, which may increase the total cross-sectional area of soft magnetic material compared to embodiments in which all wires have the same diameter. Still alternatively, in order to further minimize insulating layers 184 between the wires 183, the wires 183 may have a polygonal cross-sectional area, such as rectangular, square etc.

Figure 21I:
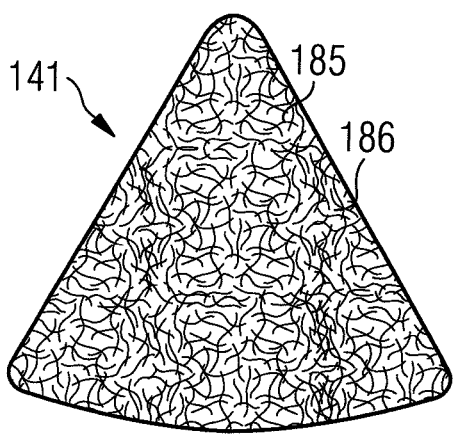
Figure 21J:
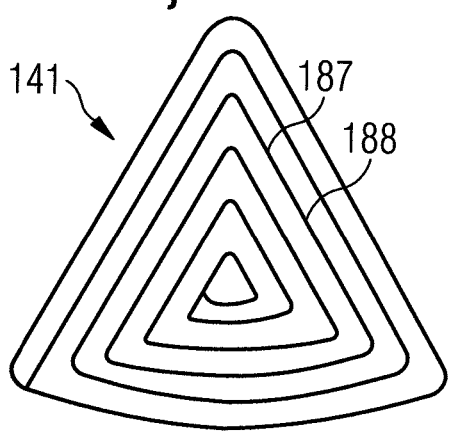

Alternatively, the discontinuous cross-section of the shaft portions 141 may be created by metal particles 185 embedded in a polymer matrix 186 as shown in FIG. 21i, or by steel wool or other porous structures impregnated with an insulating matrix. A porous and, thus, discontinuous structure of soft magnetic material may also be produced by a sintering process or high-pressure molding process, in which an insulating matrix may be omitted because insulating layers are formed automatically by oxidation of the soft magnetic material by exposure to air. Still alternatively, the shaft portion 141 may be formed of a rolled-up sheet 187 of a soft magnetic material in which the layers of the rolled-up sheet 187 are separated by insulating layers 188 as shown in FIG. 21j. This also provides a discontinuous cross-section in the sense of the present invention which reduces eddy currents in the shaft portions 141 of the posts 140.

We claim:

1. An intravascular blood pump for percutaneous insertion into a patient's blood vessel, comprising:
    a pump casing having a blood flow inlet and a blood flow outlet,
    an impeller arranged in said pump casing so as to be rotatable about an axis of rotation, the impeller having blades sized and shaped for conveying blood from the blood flow inlet to the blood flow outlet, and
    a drive unit for rotating the impeller, the drive unit comprising a plurality of posts arranged about the axis of rotation, wherein each of the posts comprises a longitudinal axis, a shaft portion extending along the longitudinal axis, and a head portion pointing towards the impeller, wherein a coil winding is disposed about the shaft portion of each of the posts, the coil windings being sequentially controllable so as to create a rotating magnetic field, wherein the impeller comprises at least one magnet arranged to interact with the rotating magnetic field so as to cause rotation of the impeller,
    wherein the shaft portion of each of the posts comprises a soft magnetic material which is discontinuous in cross-section transverse to the longitudinal axis of the respective post.

2. The blood pump of claim 1, wherein the drive unit further comprises a back plate, wherein each of the shaft portions of the posts further comprises an end, and wherein the back plate engages each of the ends of the shaft portions of the posts opposite the head portions.

3. The blood pump of claim 2, wherein the soft magnetic material is provided in the form of a plurality of sheets of the soft magnetic material.

4. The blood pump of claim 3, wherein the sheets are electrically insulated from each other.

5. The blood pump of claim 4, wherein the sheets extend parallel to the axis of rotation, so as to provide a discontinuous cross-section transverse to the axis of rotation.

6. The blood pump of claim 3, wherein the sheets have a thickness of about 25 μM to about 350 μM.

7. The blood pump of claim 3, wherein the sheets have a thickness of about 50 μM to about 200 μM.

8. The blood pump of claim 2, wherein the back plate comprises a soft magnetic material which is discontinuous in cross-section parallel to the longitudinal axis of the respective post.

9. The blood pump of claim 1, wherein the soft magnetic material is provided in the form of a first plurality of sheets of a soft magnetic material.

10. The blood pump of claim 9, wherein each of the plurality of sheets is electrically insulated from each other.

11. The blood pump of claim 10, wherein each of the plurality of sheets is electrically insulated from each other by insulating layers, each insulating layer having a thickness of about 1 μm to about 50 μM.

12. The blood pump of claim 9, wherein each of the plurality of sheets has a thickness of about 25 μm to about 350 μm.

13. The blood pump of claim 12, wherein the thickness of each of the first plurality of sheets is between about 50 μM to about 200 μM.

14. The blood pump of claim 9, wherein each of the plurality of sheets extends parallel to the longitudinal axis of the respective post.

15. The blood pump of claim 9, wherein the soft magnetic material comprises electrical steel.

16. The blood pump of claim 1, wherein the head portion of each of the posts comprises the soft magnetic material.

17. The blood pump of claim 16, wherein the soft magnetic material in the head portion is provided in the form of a second plurality of sheets, and wherein the second plurality of sheets extends in the same direction as the first plurality of sheets in the shaft portions.

18. The blood pump of claim 1, wherein each of the head portions comprises a top surface, and wherein each of the head portions of the posts extends in a plane perpendicular to the axis of rotation.

19. The blood pump of claim 18, wherein each of the top surfaces of each of the head portions, as seen in a top view in an axial direction, is aligned with the respective shaft portion in the axial direction.

20. The blood pump of claim 1, wherein the soft magnetic material is provided in the form of a plurality of wires the soft magnetic material, which are electrically insulated from each other.

21. The blood pump of claim 20, wherein the soft magnetic material comprises electrical steel.

22. The blood pump of claim 1, wherein the blood pump is an axial blood pump.

23. The blood pump of claim 1, wherein the impeller is longitudinally spaced from the drive shaft.

24. The blood pump of claim 1, wherein the impeller includes at least one magnet and wherein the drive unit is magnetically coupled to the at least one magnet disposed at an end portion of the impeller.

25. The blood pump of claim 1, wherein each coil winding is disposed about the shaft portion of a single respective post.

26. An intravascular blood pump for percutaneous insertion into a patient's blood vessel, comprising:
    a pump casing having a blood flow inlet and a blood flow outlet,
    an impeller arranged in said pump casing so as to be rotatable about an axis of rotation, the impeller having blades sized and shaped for conveying blood from the blood flow inlet to the blood flow outlet, and
    a drive unit for rotating the impeller, the drive unit comprising a plurality of posts arranged about the axis of rotation, wherein each of the posts comprises a longitudinal axis, a shaft portion extending along the longitudinal axis, and a head portion pointing towards the impeller, wherein a coil winding is disposed about the shaft portion of each of the posts, the coil windings being sequentially controllable so as to create a rotating magnetic field, wherein the shaft portion of each of the posts comprises a soft magnetic material which is discontinuous in cross-section transverse to the longitudinal axis of the respective post, wherein the soft magnetic material is provided in the form of a first plurality of sheets of a soft magnetic material, wherein the first plurality of sheets forms a stack of sheets, wherein a thickness of each of the sheets of the first plurality of sheets decreases from a central sheet at the center of the stack towards the outermost sheets of the stack.

* * * * *